(12) United States Patent
Sugahara et al.

(10) Patent No.: US 8,691,581 B2
(45) Date of Patent: Apr. 8, 2014

(54) METHOD OF MAKING DNA TAG

(75) Inventors: Junichi Sugahara, Tsuruoka (JP); Kazuhide Sekiyama, Tsuruoka (JP)

(73) Assignee: Spiber Inc., Tsuruoka-shi, Yamagata (JP)

( * ) Notice: Subject to any disclaimer, the term of this patent is extended or adjusted under 35 U.S.C. 154(b) by 0 days.

(21) Appl. No.: 13/147,128

(22) PCT Filed: Jan. 29, 2009

(86) PCT No.: PCT/JP2009/051512
§ 371 (c)(1),
(2), (4) Date: Jul. 29, 2011

(87) PCT Pub. No.: WO2010/086990
PCT Pub. Date: Aug. 5, 2010

(65) Prior Publication Data
US 2011/0281273 A1 Nov. 17, 2011

(51) Int. Cl.
*C12N 15/74* (2006.01)
*C12Q 1/68* (2006.01)
*C12P 19/34* (2006.01)
*C12N 15/00* (2006.01)

(52) U.S. Cl.
USPC ...... 435/471; 435/6.11; 435/91.1; 435/320.1; 702/20

(58) Field of Classification Search
None
See application file for complete search history.

(56) References Cited

U.S. PATENT DOCUMENTS

| | | | |
|---|---|---|---|
| 2004/0043390 A1 | 3/2004 | Stadler | |
| 2010/0248221 A1 | 9/2010 | Nasu et al. | |

FOREIGN PATENT DOCUMENTS

| | | |
|---|---|---|
| GB | 2376686 A | 12/2002 |
| JP | 2003-101485 A1 | 4/2003 |
| JP | 2008-173083 A | 7/2008 |
| WO | WO2004/009844 A1 | 1/2004 |

OTHER PUBLICATIONS

Dunn et al. (Genomic Signature Tags (GSTs): A System for Profiling Genomic DNA teach genomic DNA, Genome Research, 2002).*
The Nikkei Business Daily, Jun. 25, 2008, p. 1, (Japanese).
Nozomu Yachie et al., "Alignment-Based Approach for Durable Data Storage into Living Organisms", Biotechnol Prog., 2007, vol. 23, No. 2, pp. 501-505.
Wubin Qu et al., "MFEprimer: multiple factor evaluation of the specificity of PCR primers", Bioinformatics, (Application Note), vol. 25, No. 2, 2009, pp. 276-278.
Fumihito Miura et al., "A novel strategy to design highly specific PCR primers based on the stability and uniqueness of 3'-end subsequences", Bioinformatics, (Original Paper), vol. 21, No. 24, 2005, pp. 4363-4370.
Masanori Arita et al., "Secret Signatures Inside Genomic DNA", Biotechnol Prog., 2004, vol. 20, No. 5, pp. 1605-1607.
Dominik Heider et al., "DNA watermarks: A proof of concept", BMC Molecular Biology, 2008, vol. 9:40, pp. 1-10, (Research article).
International Search Report corresponding with International Application No. PCT/JP2009/051512 dated Mar. 3, 2009, 2 pages.

* cited by examiner

*Primary Examiner* — James Martinell
(74) *Attorney, Agent, or Firm* — Fitch, Even, Tabin & Flannery LLP

(57) ABSTRACT

Provided is a method of determining a DNA tag which is a base sequence to be introduced into a genomic DNA sequence of an organism and an introduction site of the DNA tag into the genomic DNA sequence. The method includes: a step (S1) of obtaining a protein coding sequence of the genomic DNA sequence; a step (S2) of determining a region to be treated in the protein coding sequence; a step (S3) of fragmenting the coding sequence in the region to be treated; a step (S4) of subjecting the fragmented coding sequences to a silent mutation; a step (S5) of determining sequences suitable as primers from polynucleotides including the fragmented coding sequences or complementary base sequences thereof; a step (S6) of performing a homology search for the coding sequences thus determined; and a step (S8) of determining the determined coding sequence corresponding to a minimum value of an NMS as the DNA tag, and determining the site of the fragmented coding sequence corresponding to the determined coding sequence in the protein coding sequence as the introduction site.

8 Claims, 10 Drawing Sheets

FIG. 10

```
                                                                    60
         AAACGACGGCCAGTGAATTCAAGGATATGCGAAGGTGACGTTGATTATGAGGAACCGATT
C04-J23692-59737-1-M13R(-48).ab1(1>630)
59737-1.seq(1>521)
                    10        20        30        40        50

120
         AAACGACGGCCAGTGAATTCAAGGATATGCGAAGGTGACGTTGATTATGAGGAACCGATT
         AAGGATATGCGAAGGTGACGTTGATTATGAGGAACCGATT
C04-J23692-59737-1-M13R(-48).ab1(1>630)   ↓ ↑
59737-1.seq(1>521)
                    70        80        90       100       110

180
         AATGTATCAATTCGCAATAACCACTTTGTTGGAAACGTTTCAAGTTCTGTGACCAATTTTA
         AATGTATCAATTCGCAATAACCACTTTGTTGGAAACGTTTCAAGTTCTGTGACCAATTTTA
         AATGTATCAATTCGCAATAACCACTTTGTTGGAAACGTTTCAAGTTCTGTGACCAATTTTA
C04-J23692-59737-1-M13R(-48).ab1(1>630)   ↓ ↑
59737-1.seq(1>521)
                   130       140       150       160       170

240
         ACGGGTATGGCATTTTAATAGAAGGAAATCACTCAGACAATACAATCAGCTACGGATATGG
         ACGGGTATGGCATTTTAATAGAAGGAAATCACTCAGACAATACAATCAGCTACGGATATGG
         ACGGGTATGGCATTTTAATAGAAGGAAATCACTCAGACAATACAATCAGCTACGGATATGG
C04-J23692-59737-1-M13R(-48).ab1(1>630)   ↓ ↑
59737-1.seq(1>521)
                   190       200       210       220       230

300
         GACGCAAACAGTGATCAAGGCAATATTCTGAGACGCCCGAAGATGCGGCAGCCGCGCCCCT
         GACGCAAACAGTGATCAAGGCAATATTCTGAGACGCCCGAAGATGCGGCAGCCGCGCCCCT
         GACGCAAACAGTGATCAAGGCAATATTCTGAGACGCCCGAAGATGCGGCAGCCGCGCCCCT
C04-J23692-59737-1-M13R(-48).ab1(1>630)   ↓ ↑
59737-1.seq(1>521)
                   250       260       270       280       290

360
         AGAGTCGGTATAACTGGACTGGGAGTGTCACAAGGCAAGGAAACCAGTGACGCAGTGATTG
         AGAGTCGGTATAACTGGACTGGGAGTGTCACAAGGCAAGGAAACCAGTGACGCAGTGATTG
         AGAGTCGGTATAACTGGACTGGGAGTGTCACAAGGCAAGGAAACCAGTGACGCAGTGATTG
C04-J23692-59737-1-M13R(-48).ab1(1>630)   ↓ ↑
59737-1.seq(1>521)
                   310       320       330       340       350

CAGGCAACCTCATAACCGGCTTCTCTACAGGGATTGATGTCAGGGGAAAGAGCGTTCTTGT
         CAGGCAACCTCATAACCGGCTTCTCTACAGGGATTGATGTCAGGGGAAAGAGCGTTCTTGT
         CAGGCAACCTCATAACCGGCTTCTCTACAGGGATTGATGTCAGGGGAAAGAGCGTTCTTGT
C04-J23692-59737-1-M13R(-48).ab1(1>630)   ↓ ↑
59737-1.seq(1>521)
```

FIG. 11

METHOD OF MAKING DNA TAG

CROSS-REFERENCE TO RELATED APPLICATION

This Application is a U.S. national phase application filed under 35 U.S.C. §371 of International Application No. PCT/JP2009/051512, filed Jan. 29, 2009. The entire disclosure, which includes the sequence listing(s), of International Application No. PCT/JP2009/051512 is hereby incorporated herein by reference.

TECHNICAL FIELD

The present invention relates to a method of determining a DNA sequence which shows high primer specificity in a group of unspecified DNA sequences and an introduction site of the DNA sequence into genomic DNA, and a method of introducing the sequence.

BACKGROUND ART

A treatment (cleanup) for restoring a natural environment polluted with a harmful substance to its unpolluted state, which includes no harmful substance, using a microorganism (such as a soil-improving bacterium) is called bioremediation. In the bioremediation, in order to grasp the degree of progress of the cleanup, it is essential to accurately monitor a microorganism spread in an environment. Further, it is necessary to accurately grasp the number of residual microorganism cells at a time when the cleanup is completed.

An existing procedure includes preparing total DNA in an environment (environmental DNA) where a microorganism is spread and performing a quantitative polymerase chain reaction (PCR) using, as a primer, a DNA sequence specific to the microorganism to roughly grasp the number of the microorganism cells (for example, see Non-patent Document 1). However, it is difficult to accurately grasp the number of the microorganism cells because the primer to be used in the quantitative PCR may react with non-specific DNA sequence (DNA sequences other than DNA sequences of interest in the environment, for example).

Hitherto, many reports have been made on technologies for improving primer specificity in PCR and programs for the technologies (for example, see Non-patent Documents 2 and 3). However, all the technologies are specialized for an organism which has been isolated and cultured. If the organism which has been isolated and cultured is used, probability of a reaction of the primer designed with a region other than a region to be treated can be estimated by a search of the genome. Meanwhile, in the environmental DNA in which a large indefinite number of organisms coexist, it is very difficult to estimate the specificity of the primer.

Further, the law required by the international treaty relating to a rule of handling of recombinant organisms (Cartagena Protocol) (hereinafter, sometimes referred to as "Cartagena Law") prohibits spread of recombinant microorganisms to open environments. Therefore, it is impossible to make an appropriate artificial DNA sequence which shows high primer specificity and introduce the sequence into a microorganism to be used in bioremediation or the like without careful consideration. Meanwhile, there has not been proposed a technology for introducing an artificial primer sequence into a microorganism to be used in bioremediation in such a range that the microorganism does not fall within the category "recombinant organism" specified by the Cartagena Law.

The bioremediation has advantages in that the cost and energy consumption are low as compared to a physicochemical cleanup method and that the method does not burden an ecosystem because the technology is mild, for example. On the other hand, sufficient findings on effects of spread of a microorganism for cleanup on an environment have not been obtained. Therefore, to grasp not only the degree of progress of cleanup but also the degree of dispersion of the microorganism spread and effects on the ecosystem in the field of spread as well, means for accurately monitoring has been strongly desired.

PRIOR ART DOCUMENTS

Non-patent Document 1:
  worldwide web at ritsumei.ac.jp/se/rc/staff/kubo/intro/biorem/index.html
Non-patent Document 2: Qu W, Shen Z, Zhao D, Yang Y, Zhang C (2009) MFEprimer: multiple factor evaluation of the specificity of PCR primers. Bioinformatics. 15;25:276-278.
Non-patent Document 3: Miura F, Uematsu C, Sakaki Y, Ito T (2005) A novel strategy to design highly specific PCR primers based on the stability and uniqueness of 3'-end subsequences. Bioinformatics. 15;21:4363-4370.

DISCLOSURE OF THE INVENTION

Problem to be Solved by the Invention

A main object of the present invention is to provide a technology for introducing a DNA sequence which is highly specific to a primer (hereinafter, sometimes referred to as "DNA tag") into a genome of a microorganism in an environment in which unspecified organisms coexist.

Means for Solving the Problem

The inventors of the present invention have made intensive studies to solve the above-mentioned problems, and as a result, have designed a program for selecting a DNA sequence which does not tend to be universally used by an organism and easily selecting a primer which can be universally used in environmental DNAs in which a large indefinite number of organisms coexist. The inventors of the present invention have further found that the degree of dispersion of a microorganism of interest or the degree of progress of cleanup can be detected accurately and simply by using a microorganism in which the sequence (or a complementary sequence thereof) which is used at a low frequency in the organism obtained as described above has been integrated into a genome for bioremediation and by using a primer including a sequence which is used at a low frequency in the organism. The present invention has been completed by further studies based on such findings.

The present invention provides the following method of determining a DNA tag and an introduction site.

Item 1. A method of determining a DNA tag which is a base sequence to be introduced into a genomic DNA sequence of an organism and an introduction site of the DNA tag into the genomic DNA sequence, the method including:
  a step S1 of obtaining a protein coding sequence from the genomic DNA sequence;
  a step S2 of determining a first coding sequence as a region to be treated from the protein coding sequence;
  a step S3 of obtaining a plurality of second coding sequences each including a partial sequence in the first coding sequence and having a predetermined length and recording sites of the second coding sequences in the protein coding sequence;

a step S4 of obtaining one or more third coding sequences produced by subjecting the corresponding second coding sequences obtained in the step S3 to a silent mutation;

a step S5 of judging whether or not the third coding sequences satisfy a predetermined condition and determining only the third coding sequences that satisfy the predetermined condition as fourth coding sequences;

a step S6 of performing a homology search for the fourth coding sequences and obtaining homologous base sequences;

a step S7 of determining an NMS for each of the fourth coding sequences; and a step S8 of determining the fourth coding sequence corresponding to a minimum value of the NMS as the DNA tag and determining the site of the second coding sequence corresponding to the fourth coding sequence as the introduction site, in which:

in the step 2, the first coding sequence includes a coding sequence in a region having no influence on a biological function of the organism even if the sequence is subjected to the silent mutation;

the predetermined condition includes a condition where a polynucleotide including the third coding sequence or a complementary base sequence thereof is suitable as a primer; and the NMS indicates the degree of homology.

Item 2. A method of determining a DNA tag and an introduction site according to the item 1, further including, when the fourth coding sequences having a plurality of NMS's which are the same exist, a step S9 of determining the fourth coding sequence corresponding to an NMS that appears at the minimum frequency out of the NMS's as the tag.

Item 3. A method of determining a DNA tag and an introduction site according to the item 1 or 2, in which the condition where a polynucleotide including the third coding sequence or a complementary base sequence thereof is suitable as a primer includes the following:

the complementary base sequence has a CG content of 45 to 55%;

the complementary base sequence has a tm value of 55 to 65° C.; and the complementary base sequence is free of four or more consecutive identified bases.

Item 4. A program for allowing a computer to execute a function for determining a DNA tag which is a base sequence to be introduced into a genomic DNA sequence of an organism and an introduction site of the DNA tag into the genomic DNA sequence, the program including allowing a computer to execute:

a first function for obtaining a protein coding sequence from the genomic DNA sequence;

a second function for determining a first coding sequence as a region to be treated from the protein coding sequence;

a third function for obtaining a plurality of second coding sequences each including a partial sequence in the first coding sequence and having a predetermined length;

a fourth function for obtaining one or more third coding sequences produced by subjecting the corresponding second coding sequences obtained in the third function to a silent mutation;

a fifth function for judging whether or not the third coding sequences satisfy a predetermined condition and determining only the third coding sequences that satisfy the predetermined condition as fourth coding sequences;

a sixth function for performing a homology search for the fourth coding sequences and obtaining homologous base sequences;

a seventh function for determining an NMS for each of the fourth coding sequences; and an eighth function for determining the fourth coding sequence corresponding to a minimum value of the NMS as the DNA tag and determining the site of the second coding sequence corresponding to the fourth coding sequence as the introduction site, in which:

in the step 2, the first coding sequence includes a coding sequence in a region having no influence on a biological function of the organism even if the sequence is subjected to the silent mutation;

the predetermined condition includes a condition where a polynucleotide including the third coding sequence or a complementary base sequence thereof is suitable as a primer; and the NMS indicates the degree of homology.

Item 5. A method of manufacturing a DNA-tag-introduced mutant, the method including the following steps:

(i) preparing the DNA tag determined by the method according to any one of Items 1 to 3 and cloning the DNA tag into a vector including a marker gene;

(ii) transforming a cell of an organism with the vector having the DNA tag cloned in the step (i); and (iii) removing the marker gene by continuous culture or subculture of the cell transformed in the step (ii) and obtaining a mutant having the DNA tag introduced into a genome through homologous recombination.

Item 6. A method according to the item 5, further including the step of confirming that the marker gene is absent in the genome of the organism.

Item 7. A mutant, which is obtained by the method according to the item 5 or 6.

Item 8. A vector, including a DNA tag determined by the method according to any one of Items 1 to 3.

Item 9. A genomic DNA, including a DNA tag introduced by the vector according to the item 8.

Item 10. A mutant, including the genomic DNA according to the item 9.

Item 11. A method of monitoring progress of cleanup by quantifying the number of mutants each including a DNA tag determined by the method according to any one of Items 1 to 3 in an environment using a primer including a polynucleotide having a base sequence of the DNA tag or a complementary base sequence thereof.

Item 12. A method of evaluating diffusion of a mutant including a DNA tag determined by the method according to any one of Items 1 to 3 in an environment using a primer including a polynucleotide having a base sequence of the DNA tag or a complementary base sequence thereof.

Item 13. A method of labeling an organism, the method including introducing a DNA tag determined by the method according to any one of Items 1 to 3 into genomic DNA of an organism using a vector having the DNA tag cloned thereinto.

Effects of the Invention

According to the method of the present invention, it is possible to artificially make the DNA sequence (sometimes referred to as "DNA tag") which rarely appears in a natural environment. A primer having such DNA sequence (or a complementary strand thereof) can drastically improve primer specificity in quantitative PCR to be used, for example, for grasping the number of microorganism cells in the field of bioremediation or the like and can accurately and simply grasp the degree of progress in cleanup and the degree of dispersion of a microorganism.

As mentioned above, the Cartagena Law forbids spread of a recombinant microorganism to an open environment. However, a recombinant obtained by self-cloning (including a silent mutation) does not fall within the category "recombinant organism" specified by the Cartagena Law. Therefore, a mutant, which does not undergo any alteration to a genomic DNA sequence in a cell other than a region into which the DNA tag is introduced, does not conflict with the Cartagena Law and can also be used in the open environment. That is, according to the method of the present invention, it is possible to introduce the DNA tag into a genome of an organism so that the recombinant does not fall within the category "recombinant organism" specified by the Cartagena Law.

Meanwhile, for example, if the thus obtained microorganism including the DNA tag introduced is used for bioremediation, the microorganism can be monitored at high accuracy.

BRIEF DESCRIPTION OF THE DRAWINGS

FIG. 10 is a diagram illustrating results of sequencing (first half of SEQ ID NO.: 18) performed in Reference Test Example II.

FIG. 11 is a diagram illustrating results of sequencing (latter half of SEQ ID NO.: 18) performed in Reference Test Example II.

MODES FOR CARRYING OUT THE INVENTION

Hereinafter, the present invention is described in detail.

(1) Method of Determining DNA Tag and Introduction Site

Hereinafter, embodiments according to the present invention are described based on the accompanying drawings.

Figure 1:
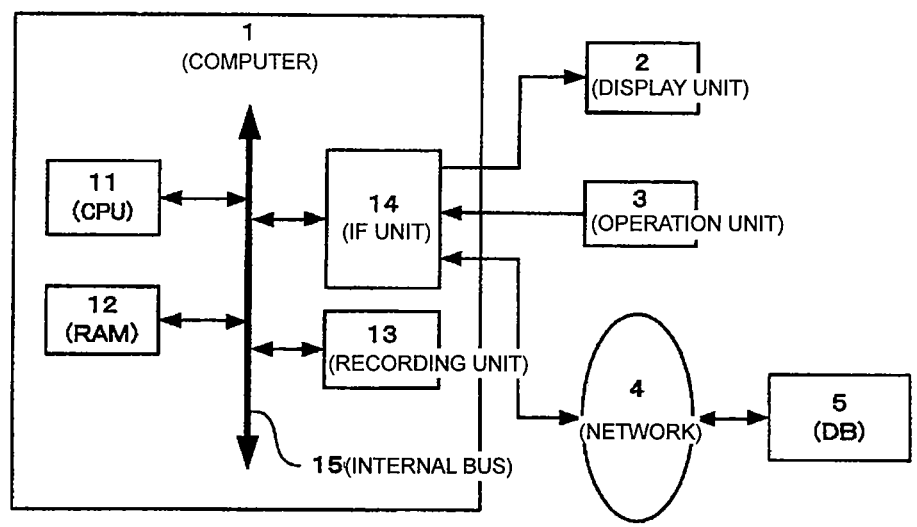
FIG. 1 is a block diagram illustrating a configuration of a device to be used in a method of determining a tag and an introduction site according to an embodiment of the present invention.

FIG. 1 illustrates a block diagram illustrating a configuration of a device to be used for a method of determining a DNA tag and an introduction site thereof according to an embodiment of the present invention. Here, the "DNA tag" refers to a DNA sequence which rarely appears in a natural environment (the sequence is a DNA sequence that may be a positive strand or an opposite strand, and the sequence per se or a complementary sequence thereof is used as a "primer"). The "introduction site" of the DNA tag refers to a site in a DNA sequence of an organism into which the DNA tag is introduced (the DNA tag is substituted for a partial sequence).

In the present invention, the species of the organism into which the DNA tag is introduced is not particularly limited as long as the organism has a DNA where the tag can be introduced by a known method, and examples thereof include prokaryotes, archaea, and eukaryotes. In the present invention, it is preferred to use a microorganism such as *Escherichia coli, Bacillus subtilis*, or yeast which is known for its culture condition and storage condition and which can be stored for a relatively long period of time. Moreover, a microorganism to be used for environmental cleanup is preferably used because the microorganism can be easily monitored when used in bioremediation. Examples thereof include bacteria each having an ability to degrade petroleum, bacteria each having an ability to degrade a variety of harmful chemical substances, and bacteria which absorb salts in environments. Specific examples thereof include: *Bacullus* bacteria such as *Bacullus* sp. ODM157 and *Bacullus* sp. ODNM4, *Bacullus* sp. F31; *Rhodococcus* bacteria such as *Rhodococcus* sp. ODNM2B, *Rhodococcus* sp. NDMI144, *Rhodococcus* sp. NDKK48, *Rhodococcus* sp. NDKK7, *Rhodococcus* sp. NDKK6, *Rhodococcus* sp. NDKK5, *Rhodococcus* sp. NDKK2, *Rhodococcus* sp. NDKK1, *Rhodococcus* sp. NDMI54, *Rhodococcus* sp. ODNM1C, *Rhodococcus* sp. NDKY3D, and *Rhodococcus* sp. NDKY72A; *Gordonia* bacteria such as *Gordonia* sp. NDKY76A, *Gordonia* sp. NDKK46, *Gordonia* sp. NDKY2B, and *Gordonia* sp. NDKY2C; *Acientobacter* bacteria such as *Acientobacter* sp. ODYM1, *Acientobacter* sp. ODYM2, *Acientobacter* sp. ODYM5, *Acientobacter* sp. ODDK71, *Acientobacter* sp. ODMI29, *Acientobacter* sp. ODNM6, *Acientobacter* sp. NDMI119, *Acientobacter* sp. A132, *Acientobacter* sp. NDMI78, and *Acientobacter* sp. YM3; and *Pseudomonas* bacteria such as *Pseudomonas* sp. F721 and *Pseudomonas* sp. F722. Meanwhile, the present invention also includes introduction of a DNA sequence tag into a plasmid.

This device includes a computer 1, a display unit 2, and an operation unit 3. Examples of the display unit 2 include a liquid-crystal display device and a CRT display device. Examples of the operation unit 3 include a keyboard and a mouse for computer. The computer 1 includes a processing unit (hereinafter, referred to as "CPU") 11, a rewritable memory 12 capable of temporarily storing data (hereinafter, referred to as "RAM"), a recording unit 13 such as a rewritable hard disk drive capable of continually storing data, an interface unit (hereinafter, referred to as "IF unit") 14, and an internal bus 15. In the recording unit 13, a program and data performed by the CPU 11 are recorded. The IF unit 14 plays a role as an interface between the computer 1 and an external apparatus. That is, the CPU 11 allows the display unit 2 to display processing results or the like via the IF unit 14, and in the case where the operation unit 3 is operated by, for example, a man, information relating to the operation is obtained via the IF unit 14. Meanwhile, the computer 1 is connected to a network 4 via the IF unit 14. The network 4 may be a public network such as internet or a local network. A database (hereinafter, referred to as "DB") 5 where genomic DNAs are recorded is also connected to the network 4. The respective components of the computer 1 exchange the data via the internal bus 15. This procedure enables the computer 1 to perform not only the arithmetic processing of the computer itself but also processing such as acquirement of instructions from the operation unit 3 or use of DB5. FIG. 1 illustrates one DB5, but the apparatus may have a plurality of DBs.

Figure 2:
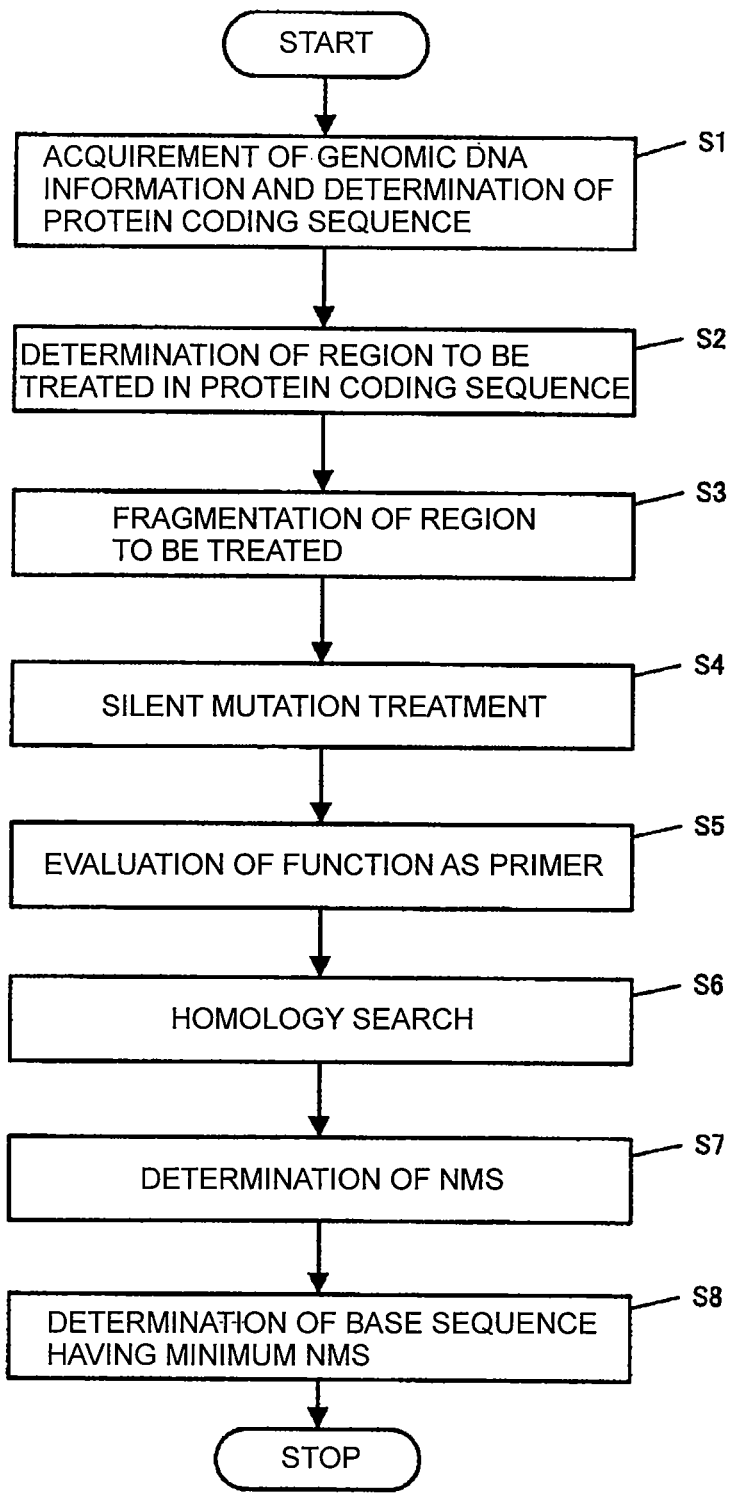
FIG. 2 is a flow chart illustrating a method of determining a tag and an introduction site according to an embodiment of the present invention.
Figure 3:
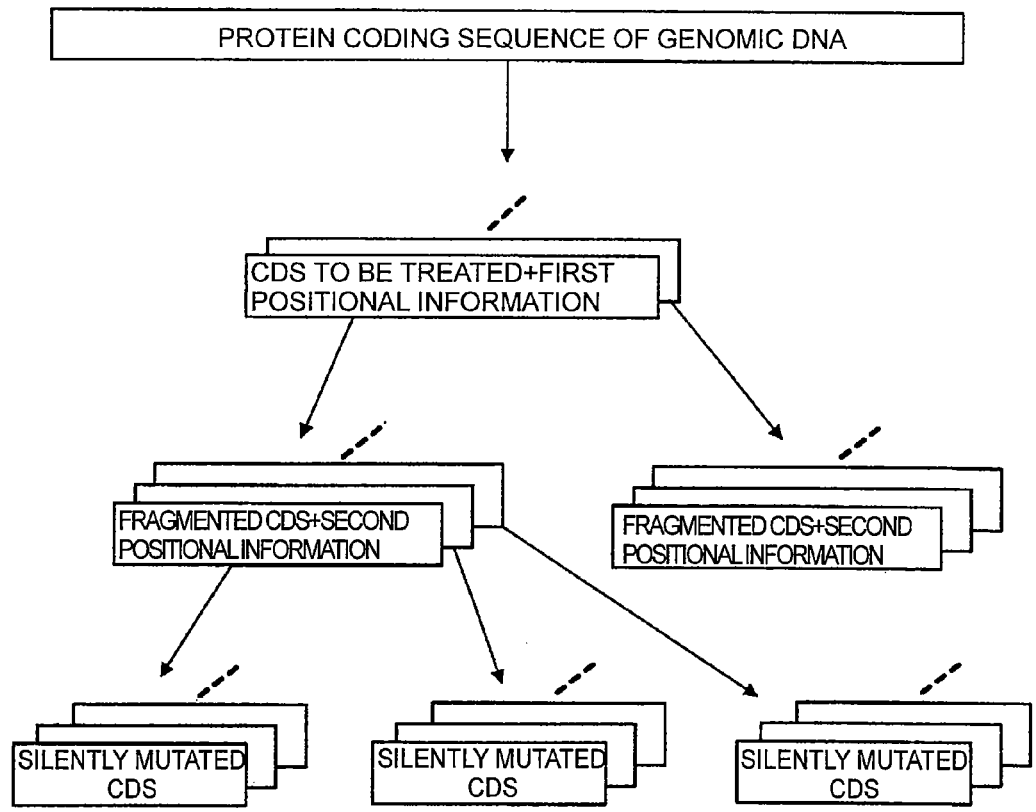
FIG. 3 is a diagram illustrating a relationship of CDSs to be produced.

Next, a specific description is made on the method of determining the tag and introduction site of the tag according to the embodiment of the present invention with reference to the flow chart illustrated in FIG. 2. In addition, FIG. 3 is a block diagram illustrating a relationship of sequences prepared by treatment as mentioned below.

Hereinafter, the processing is performed by the CPU 11 unless otherwise specified. Further, the CPU 11 appropriately reads necessary data from the recording unit 13 to the RAM 12, performs processing using a predetermined region of the RAM 12 as a work region, and appropriately records temporary processing results or final processing results in the recording unit 13. In addition, initial data is recorded in advance in the recording unit 13.

In a step S1, genomic DNA, i.e., a base sequence (single-stranded sequence) information of the organism where the tag is introduced is obtained. For example, genomic DNA information recorded in advance in the recording unit 13 (for example, text data) is read out. Alternatively, the genomic DNA information may be obtained from DB5.

Figure 4:
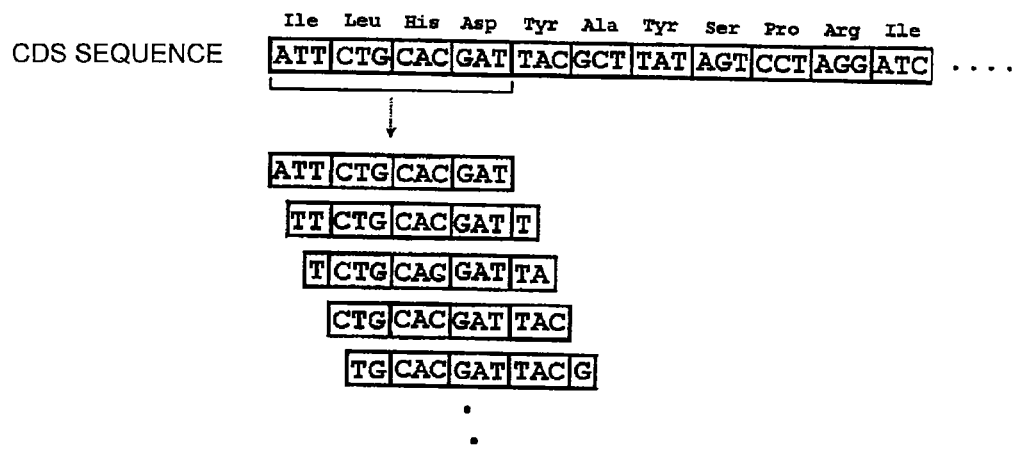
FIG. 4 is a diagram illustrating a relationship between a CDS (SEQ ID NO.: 9), encoding SEQ ID NO.: 8) to be treated and fragmented CDSs (fragments of SEQ ID NO.: 9).

From the genomic DNA information thus obtained, all DNA sequence regions encoding proteins (CDSs: Coding Sequences) are determined. A query is performed for existing DB5 to perform annotation of the CDS, i.e., determination of a DNA region (positional information) encoding the protein using CDS information, if present, or by a known informational procedure. The top of FIG. 3 illustrates a determined protein CDS. FIG. 4 illustrates a more specific example of the CDS. In FIG. 4, each codon in the base sequence is surrounded by a square, and amino acids encoded are illustrated on the respective squares.

In a step S2, regions to be treated in the following steps are determined from all the protein coding sequences determined in the step S1. That is, a region which is considered to have a large effect on proliferation or phenotype of the host cells (organisms) by addition of the silent mutation is excluded from the protein coding sequences. Examples of the regions to be excluded include the whole sequences of essential genes, functional sequences, and sequences which are located at near a translation starting point and are considered to be significantly involved in control of efficiency of protein translation (about 50 bases located on the downstream), and a sequence located at near a stop codon (about 50 bases located on the upstream). Further, in the case of organisms having industrial values, examples thereof include genes which may impair the industrial values by mutations (for example, in the case of microorganisms capable of producing useful substances, examples thereof include the whole sequences of genes which are directly involved in production of the useful substances). Examples of the functional sequences include sequences which recognize restriction enzymes and sequences which recognize nucleic acid binding proteins. Therefore, usually, a plurality of CDSs to be treated having different lengths are determined. The thus-determined protein coding sequences are sometimes referred to as "CDSs to be treated" (or "first coding sequences"). FIG. 3 illustrates the determined CDS to be treated.

The determined CDSs to be treated are recorded in the recording unit 13 in relation to the genomic DNA information. In this procedure, the positional information of the CDSs to be treated in the protein coding sequence (hereinafter, also referred to as "first positional information") is also recorded in the recording unit 13 in relation to the CDS to be treated. That is, the {genomic DNA information, CDS to be treated, and first positional information} are recorded as one set.

In a step S3, each of the CDSs to be treated determined in the step S2 is fragmented into a designated size. That is, a continuous CDS having a predetermined length (hereinafter, also referred to as "fragmented CDS" or "second coding sequence") is selected from the CDSs to be treated. For example, as illustrated in FIG. 4, fragmented CDSs each having a designated size (for example, 12 bases) are selected with shifting the starting position one base by one base. Therefore, in the case where each fragmented CDS includes m base sequences (designated size: m), n−m+1 fragmented CDSs are determined from one CDS to be treated which includes n base sequences. FIG. 3 illustrates the fragmented CDSs determined. It should be noted that this procedure does not judge whether or not a plurality of the same fragmented CDSs are produced. This is because even if the same fragmented CDSs are used, final sequences produced by the silent mutation may be different depending on insertion sites into a target organism (that is, depending on the upstream and downstream sequences in the fragmented CDS). In addition, if the upstream and downstream sequences are the same, this procedure does not limit one sequence because the positional information from which the fragmented CDSs are obtained becomes an important factor in the future. It should be noted that a plurality of the same fragmented CDSs are less likely to be produced.

The size of each of the fragmented CDSs may be arbitrarily set as long as the size is a length which allows the CDSs to act as primers. Usually, the size is desirably 15 to 30 bases, more desirably 17 to 25 bases.

In this procedure, the original CDS to be treated from which the fragmented CDSs are produced, and positional information of the fragmented CDSs in the CDS to be treated (hereinafter, also referred to as "second positional information") are recorded in the recording unit 13 in relation to the fragmented CDSs. That is, the {CDS to be treated, fragmented CDSs, and second positional information} are recorded as one set. Therefore, if one fragmented CDS is designated, the second positional information corresponding to the sequence, and the CDS to be treated and first positional information corresponding to the sequence are determined. From the first positional information and second positional information, the position of the fragmented CDS in the genome sequence is specified.

In a step S4, each of the fragmented CDSs determined in the step S3 is subjected to the silent mutation, to thereby obtain one or more silently mutated CDSs (hereinafter, also referred to as "third coding sequences"). That is, CDSs are prepared by substituting synonymous codons (which have different base sequences but are translated into the same amino acid) for codons in each fragmented CDS. For example, in the case where one fragmented CDS includes ATTCTGCACGAT (nucleotides 1-12 of SEQ ID NO.: 9) and the position of the base sequence on the 5'-end of a protein coding sequence to be treated is 0, if the position of the base on the 5'-end of the fragmented CDS of the protein coding sequence to be treated is a multiple of three (calculated from the first and second positional information), the sequence includes four complete codons and is translated into the amino acids: Ile-Leu-His-Asp. For the amino acids, there are synonymous codons as shown in Table A.

TABLE A

| Amino acids | Synonymous codons |
|---|---|
| Ala | GCU, GCC, GCA, GCG, |
| Arg | AGA, AGG, CGU, CGC, CGA, CGG |
| Asn | AAU, AAC |
| Asp | GAU, GAC |
| Cys | UGU, UGC |
| Gln | CAA, CAG |
| Glu | GAA, GAG |
| Gly | GGU, GGC, GGA, GGG |
| His | CAU, CAC |
| Ile | AUU, AUC, AUA, |
| Leu | CUU, CUC, CUA, CUG, UUA, UUG |
| Lys | AAA, AAG |
| Phe | UUU, UUC |
| Pro | CCU, CCC, CCA, CCG |
| Ser | AGU, AGC, UCU, UCC, CUA, CUG |
| Thr | ACU, ACC, ACA, ACG |
| Tyr | UAU, UAC |
| Val | GUU, GUC, GUA, GUG |

Therefore, in the case of the above-mentioned example, there are 3×6×2×2=72 possible sequences which include codons encoding four amino acids. Of those, sequences including at least one original codon (specifically, ATT, CTG, CAC, and GAT) are excluded, and hence there are 2×5×1×1=10 sequences. For example, from a fragmented CDS including ATTCTGCACGAT (nucleotides 1-12 of SEQ ID NO.: 9), silently mutated CDSs such as ATCTTACATGAC (SEQ ID NO.: 15) and ATACTCCATGAC (SEQ ID NO.: 19) are produced.

Meanwhile, in the case where one fragmented CDS includes ATTCTGCACGAT and the position of the base sequence on the 5'-end of the protein coding sequence is 0, if the position of the base on the 5'-end of the fragmented CDS in the protein coding sequence to be treated is not a multiple of three, the fragmented CDS is a sequence including three complete codons and two incomplete codons (because of lack of base information of the first and last codons). In this case, deficient bases in the two incomplete codons can be supplied with reference to genomic DNA information recorded in the recording unit 13.

In this procedure, to decrease the homology to the sequence before introduction of the silent mutation as much as possible, it is desirable to exclude fragmented CDSs including codons before introduction of the mutation and to add the silent mutation as much as possible.

The silently mutated CDSs thus produced are recorded in the recording unit 13 in relation to the original fragmented CDSs. That is, the {silently mutated CDS, and fragmented CDSs} are recorded as one set.

Meanwhile, the silent mutation may be introduced into one or more codons which form the fragmented CDSs, but preferably, the silent mutation is introduced into all codons which form the fragmented CDSs. In each codon, the silent mutation may be introduced into only any base into which the silent mutation can be introduced, more preferably only the third base. However, from the point of view of improvement of primer specificity, it is preferred to introduce all the silent mutations into the fragmented CDSs.

Meanwhile, for example, usage of all codons in genomic DNA of an organism where the tag is introduced may be calculated in advance, and based on the information, use of codons which are very less frequently used in the genomic DNA of the organism where the tag is introduced may be avoided at the time of introduction of the silent mutations.

In a step S5, functions of polynucleotides including the silently mutated CDSs per se produced in the step S4 or complementary base sequences thereof as primers are evaluated, and silently mutated CDSs which do not satisfy predetermined criteria are excluded. The exclusion can be performed by setting a flag added to each fragmented CDS to a value (e.g., "1") different from the initial value (e.g., "0"). In this procedure, the {silently mutated CDS, fragmented CDSs, and flag} are recorded as one set.

Examples of evaluation criteria of functions of the nucleotides as primers include the following conditions (a) to (c):
  (a) the nucleotide has a GC content of 40 to 60%, preferably 45 to 55%;
  (b) the nucleotide has a tm value of 55 to 65° C.; and/or
  (c) the nucleotide does not have five or more, preferably four or more of consecutive identical bases.

If a silently mutated CDS per se or a complementary base sequence thereof does not satisfy one or more of the conditions, the silently mutated CDS is excluded.

Here, the GC content is a ratio (%) of the number of GC bases in a base sequence. The tm value is a temperature (melting temperature) at which 50% of double-stranded DNAs dissociate into single-stranded DNAs. Methods of calculating the GC content and tm value are known, and hence detail descriptions of the methods are omitted. It should be noted that the criterion values may be recorded in advance as initial data in the recording unit 13, but may be designated from outside via the IF unit. Further, the evaluation criteria of the primers may be known ones and are not limited to the above-mentioned conditions (a) to (c).

The silently mutated CDSs having functions as primers in this step S5 are sometimes referred to as "fourth coding sequences".

In a step S6, the silently mutated CDSs remaining after the step S5 (fourth coding sequence; that is, the flag is "0") is subjected to a homologous search for a genome sequence database previously prepared depending on purposes using a sequence alignment procedure. For example, if the resultant primers are used for bioremediation, the homologous search is performed for an environmental DNA database for bioremediation using a BLAST method. More specifically, searches are performed on a genome database provided by DDBJ, GENBANK, or the like, or a database storing fragmented base sequences of genes or the like using gene homology search software including Blast algorism or the like, and in the case where there is a region having homology equal to or higher than a threshold, the score of the homology is recorded (the score of the homology may be, for example, a ratio of the number of matched bases to the length of the silently mutated CDS. For example, in the BLAST method, an index such as Identity corresponds to the score). Meanwhile, the number of regions having homology equal to or higher than the threshold is counted. It should be noted that the threshold of the homology may be set so that the ratio of the number of matched bases to the length of the query base is, for example, 80% or more, preferably 50% or more, more preferably 20% or more, still more preferably 10% or more when a gap is not taken into account. In addition, the homology search can be performed not only by the BLAST method but also by a known method such as a FASTA method.

In a step S7, appearance frequency and Nearest Match Score (NMS) of each silently mutated CDS are determined using the results of the homology search performed in the step S6, that is, responses (response data) from the database to the genome sequence database for query. In this procedure, the homology search may be performed by a variety of known methods, and one of the methods may be used. Detail descriptions of the methods are omitted here. Hereinafter, a region having 50% or more homology is defined as a homologous region. Meanwhile, the genome sequence database used may be produced from a database provided by National Center of Biotechnology Information (NCBI) in USA depending on the purpose. In addition, a variety of genome sequence databases are known and may be used.

The appearance frequency is the number of genomes hit (the homologous region has been detected) by the homology search. Therefore, the initial value of the appearance frequency of a specific silently mutated CDS is defined as "0", and if there is a genome hit by the homology search, the appearance frequency is increased by "1". However, even in the case where a plurality of regions are hit in one genome, the appearance frequency is increased by "1". The NMS is the maximum homology value when a plurality of regions are hit.

Figure 5:
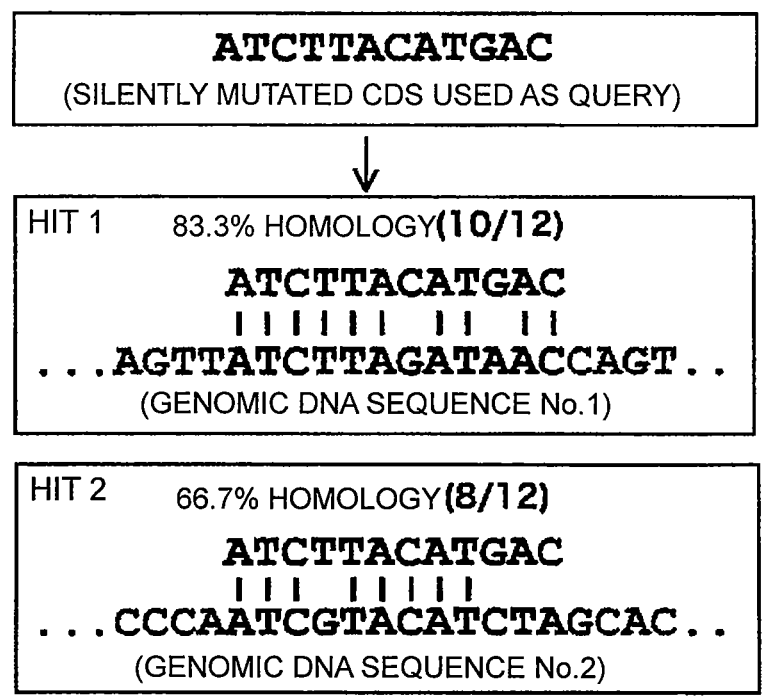
FIG. 5 is a diagram illustrating one example of a silently mutated CDS (SEQ ID NO.: 15) and results of a homology search using the sequence.

More detail descriptions are shown below. FIG. 5 illustrates ATCCATCATGAC SEQ ID NO.: 20 as one example of the silently mutated CDSs. It is assumed that two homologous regions (hits 1 and 2) to the silent mutated CDS are obtained by the homology search on a database. In FIG. 5, the hit 1 is a partial sequence of ATCTTAGATAAC (SEQ ID NO.: 21) in the first genomic DNA sequence No. 1, and the hit 2 is a partial sequence of ATCGTACATCTA (SEQ ID NO.: 22) in the second genomic DNA sequence No. 2 (different from the first genomic DNA sequence). In this case, the identity of the hit 1 is 83.3%, while the identity of the hit 2 is 66.7%. Therefore, the identity 83.3% of the hit 1 having the maximum identity is defined as an NMS of the silently mutated CDS. In addition, the appearance frequency of the silently mutated CDS is "2". It should be noted that, as mentioned below, in the case where the NMSs are the same for a plurality of different silent mutations, the appearance frequency is used as a screening index for determining a sequence which does not appear in a natural environment.

As a result, the NMS and appearance frequency for one silently mutated CDS are determined and are recorded in the recording unit 13 so that the information is in relation to each other. That is, the {silently mutated CDS, NMS, and appearance frequency} are recorded as one set.

In a step S8, the minimum value of the NMSs recorded in the step S7 is determined, a silently mutated CDS corresponding to the value is determined as a tag, and from positional information corresponding to the sequence, an introduction site (site in the genomic DNA sequence) is determined. The tag and introduction information determined are displayed in the display unit 2, for example.

If there is one minimum NMS, the silently mutated CDS corresponding to the value is determined as the tag. However, in the case where the NMSs are the same value for a plurality of different silent mutations, a step of determining a silently mutated CDS having the minimum appearance frequency is determined as the tag as a step S9. This is because an object of the present invention is to determine a sequence (tag, primer) which does not appear in a natural environment.

According to the above-mentioned procedures, it is possible to determine the tag which is highly likely to be used universally even in environmental DNAs in which a large indefinite number of organisms coexist and the introduction site into the genomic DNA sequence. Therefore, a complementary base sequence of the tag can be used as a primer having high specificity in quantitative PCR.

Is should be noted that the invention of the present application is not limited to the above-mentioned embodiments and may be modified by changing the order of the treatments, eliminating a part of the treatments, or substituting another treatment for a part of the treatments, or the like.

For example, the above-mentioned description shows the case where the genomic DNA of one organism is treated, but in the case where the genomic DNAs of a plurality of organisms are treated, the treatments of the step S1 to S8 may be performed for each genomic DNA.

Moreover, in the step S2, a region to be excluded may be designated from the outside.

Further, the step S2 may include not only excluding a region which is considered to largely affect host cells (organism) by the silent mutation but also excluding another region. Specifically, examples thereof include a region encoding a protein having unknown functions and a region encoding a protein having functions important for achieving the purpose (such as an enzyme capable of degrading petroleum in the case where the present invention is used for bioremediation). If the number of CDSs to be treated is large, the treatment requires longer time because the number of the fragmented CDSs and silently mutated CDSs becomes larger. Therefore, to reduce the treatment time, the number of the CDSs to be treated may be reduced as far as a certain level of accuracy can be achieved, and usually, about 50 to 1,000 CDSs are treated.

Further, the above-mentioned descriptions show the case where, in the step S3, the fragmented CDSs are determined by shifting the position of the top of a coding sequence having a predetermined length one by one, but regions having continuous predetermined lengths may be selected at random so that the regions do not overlap with each other, to thereby obtain a plurality of fragmented CDSs.

Moreover, the criteria for evaluation of functions as primers in the step S5 are not limited to the above-mentioned ones. For example, instead of the condition (c), or in addition to the conditions (a) to (c), a condition where the base on the end is G or C may be added. That is, a sequence where the base on the end is A or T may be excluded from an object to be treated.

Further, in the homology search in the step S6, the degree of the homology may be designated from the outside instead of use of a predetermined degree of the homology (50% or more in the above-mentioned case).

Further, although the above-mentioned descriptions show the case where the NMS and appearance frequency are used as criteria of the output in the step S7, the criteria are not limited thereto, and the GC content or the like may be considered. In general, primers to be used in PCR preferably have GC contents of about 55 to 65%.

In addition, the primers more preferably include G and C in large amounts on the 3'-end side. Moreover, in PCR, a bond between the 3'-end on the primer side and the 5'-end on the DNA side is important, and hence candidates having a smaller number of matches in the regions corresponding thereto (the number of homologous bases detected by alignment) are more preferred. Depending on the purpose, final candidates may be determined on the basis of the criteria.

(2) Method of Manufacturing DNA Tag-Introduced Mutant

A mutant into which the DNA tag determined by the above-mentioned method of determining the DNA tag and introduction site has been introduced may be obtained based on a known genetic engineering procedure, and for example, the mutant may be obtained as follows.

A method of manufacturing a DNA-tag-introduced mutant including the following steps:

(i) preparing the DNA tag determined by the method of determining a DNA tag and an introduction site and cloning the DNA tag into a vector including a marker gene;

(ii) transforming a cell of an organism with the vector having the DNA tag cloned in the step (i); and (iii) removing the marker gene by continuous culture or subculture of the cell transformed in the step (ii) and obtaining a mutant having the DNA tag introduced into a genome through homologous recombination.

Hereinafter, the respective steps are described in detail. It should be noted that a method of manufacturing a mutant based on homologous recombination by single crossover is described here as an example.

In the step (i), the DNA tag determined by the method of determining a DNA tag and an introduction site is prepared and cloned into a vector.

To determine the base sequence of the DNA tag to be introduced into cells and the introduction site of the base sequence, first, the steps S1 to S8 are performed as mentioned above. To synthesize DNA fragments based on the resultant DNA tag sequence, a conventionally known synthesizer may be used.

To clone the DNA tag into the vector, (m) a DNA including a base sequence corresponding to the first coding sequence may be synthesized and integrated into the vector, and then a silent mutation may be introduced into a predetermined site by a point mutation introduction method. Alternatively, (n) a DNA including a base sequence corresponding to the fourth coding sequence (DNA tag) may be synthesized and integrated into the vector.

The point mutation introduction method may be performed in accordance with a conventionally known method such as GeneTailor Site-Directed Mutagenesis System (Invitorogen) KOD-Plus-Mutagenesis Kit (TOYOBO).

It should be noted that the vector is desirably constructed by using a bacterium other than a target bacterium into which the DNA tag is introduced. Moreover, the transformation of host cells is performed by homologous recombination, and hence upstream and downstream base sequences each including a region into which the DNA tag sequence is introduced are constructed on the vector. The length of the former sequence of the DNA tag is appropriately set depending on efficiency of the homologous recombination of the bacterial strain where the tag is introduced, and the lengths of the upstream and downstream sequences are preferably 50 bases or more, more preferably 200 bases or more, still more preferably 500 bases or more. When the regions are constructed on the vector, the regions may be obtained by PCR using genomic DNA of target host cells as a template. In this procedure, the upstream/downstream regions of the first coding region are obtained so that the base sequence corresponding to the first coding sequence is included, and then introduction of the point mutation may be performed on the vector (corresponding to the item (m)). Further, a base sequence obtained by replacing the first coding sequence sites on the upstream/downstream regions including the base sequence corresponding to the first coding sequence with a base sequence corresponding to the fourth coding sequence may be synthesized by a known artificial gene construction method (such as overlap extension PCR) and constructed on the vector (corresponding to the item (n)).

According to the above-mentioned method, a mutant including only the DNA tag introduced into the genome by homologous recombination in the step (iii) mentioned below can be obtained.

The vector preferably includes a marker gene so that the gene can be expressed in cells into which the DNA tag is introduced, and examples of the marker gene include an antibiotic-resistant marker gene, a gene encoding a fluorescent protein, and a gene encoding an enzyme which catalyzes a coloring reaction.

In the present invention, the antibiotic-resistant marker gene may be appropriately selected from conventionally known ones as long as the host cells have no antibody against the antibiotic, and the gene can be used as a marker. Specific examples of the antibiotic-resistant marker include ampicillin-resistant gene, streptomycin-resistant gene, tetracycline-resistant gene, erythromycin-resistant gene, puromycin-resistant gene, blasticidin S-resistant gene, hygromycin-resistant gene, kanamycin-resistant gene, gentamicin-resistant gene, chloramphenicol-resistant gene, and neomycin-resistant gene. Examples of the gene encoding a fluorescent protein include green fluorescent protein (GFP) gene, red fluorescent protein (RFP) gene, yellow fluorescent protein (YFP) gene, and luciferase gene. Examples of the gene encoding an enzyme which catalyzes a coloring reaction include β-glucuronidase (GUS) gene and lacZ gene.

To integrate the marker gene into the vector so that the gene can be expressed, known promoter and terminator may be appropriately added depending on the type of the host cells. In the case where the promoter and terminator of the host cells are unknown, the sequences thereof may be determined before use in accordance with a conventionally known informatics procedure.

The synthesized DNA fragments may include not only a region encoding the sequence of the DNA tag but also a variety of regions. Examples of the region include: introduction of a transcription-terminating sequence; introduction of a known restriction enzyme-recognizing sequence for cleaving the site; and introduction of a methylase-recognizing sequence.

The synthesized DNA fragments may be introduced into target cells after the fragments are inserted into an appropriate vector. The vector can be appropriately selected depending on the type of cells into which the vector is introduced. Examples of the vector include: plasmid DNAs including YCp-type *Escherichia coli*-yeast shuttle vectors such as pRS413, pRS414, pRS415, pRS416, YCp50, pAUR112, and pAUR123, YEp-type *Escherichia coli*-yeast shuttle vectors such as pYES2 and YEp13, YIp-type *Escherichia coli*-yeast shuttle vectors such as pRS403, pRS404, pRS405, pRS406, pAUR101, and pAUR135, plasmids derived from *Escherichia coli* (e.g., ColE-type plasmids such as pBR322, pBR325, pUC18, pUC19, pUC118, pUC119, pTV118N, pTV119N, pBluescript, pHSG298, pHSG396, and pTrc99A, p15A-type plasmids such as pACYC177 and pACYC184, and pSC101-type plasmids such as pMW118, pMW119, pMW218, and pMW219), plasmids derived from *Agrobacterium* (e.g., pBI101), and plasmids derived from *Bacillus subtilis* (e.g., pUB110 and pTP5); phage DNAs including λ phages (Charon4A, Charon21A, EMBL3, EMBL4, λgt10, λgt11, and λ ZAP), φX174, M13 mp 18, and M13 mp 19; retrotransposons including a Ty factor; and YAC vectors including pYACC2. In addition, there can be also used animal virus vectors such as a retrovirus and a vaccinia virus, and insect virus vectors such as a baculovirus.

It should be noted that the present invention may include a vector including the above-mentioned DNA tag cloned.

In this step, the on sequence in the vector to be introduced desirably does not act in an organism into which the DNA tag is introduced. In the case of using a shuttle vector to be used between a host organism in which the vector is constructed and an organism into which the DNA tag is introduced, the ori sequence for the organism into which the DNA tag is introduced is desirably removed in advance. The on sequence is also called a replication starting point, and in the case where the vector has the sequence, replication is performed in the host cells into which the DNA tag is introduced. If the vector can be replicated in cells of a target organism in transformation of the organism by homologous recombination in the step (ii), selection using the marker gene may cause appearance of not only a mutant of interest but also a bacterial strain selected because the strain has the vector. In the step (ii), it is desirable to obtain a mutant which is transformed into the genome of the organism by homologous recombination and has no vector in the cells, and hence, it is desirable to use a vector including no on sequence or to remove the on sequence of the vector in advance. However, in the case where the on sequence of a host organism (such as *Escherichia coli*) in which the vector is constructed does not act as a replication-starting point in the organism into which the DNA tag is introduced, it is not necessary to remove the ori sequence.

In the step (ii), transformation by homologous recombination is performed at a predetermined site on genomic DNA of cells using a vector including the DNA tag cloned, to thereby obtain cells which have been transformed into the genome by homologous recombination based on single crossover.

As a transformation method, a conventionally known procedure may be employed. For example, in the case where the cells are plant cells, the above-mentioned vector may be introduced into the plant cells by a usual transformation method such as a vacuum wet method (agrobacterium method), a particle gun method, a PEG method, or an electroporation method. Tumor tissues, shoots, hairy roots, or the like obtained by such method may be used for cell culture, tissue culture, or organ culture without further treatment and can be regenerated into plant bodies by administration of appropriate concentrations of phytohormones (such as auxin, cytokinin, gibberellin, abscisic acid, ethylene, and brassinolide) using conventionally known methods for plant tissue culture. Meanwhile, in the case where the vector is introduced into a bacterium such as *Escherichia coli* or *Bacillus subtilis*, for example, a method involving using a calcium ion [Cohen, S, N. et al.: Proc. Natl. Acad. Sci., USA, 69:2110 (1972)] or an electroporation method may be employed. Further, in the case where the vector is introduced into yeast, for example, an electroporation method [Becker, D. M. et al.: Methods. Enzymol., 194: 182 (1990)], a spheroplast method [Hinnen, A. et al.: Proc. Natl. Acad. Sci., USA, 75: 1929 (1978)], or a lithium acetate method [Itoh, H.: J. Bacteriol., 153:163 (1983)] method may be employed. Further, in the case where the vector is introduced into animal cells, for example, an electroporation method, a calcium phosphate method, or a lipofection method may be employed. In the case where the vector is introduced into insect cells, for example, a calcium phosphate method, a lipofection method, or an electroporation method may be employed.

As mentioned above, a combination including: a plasmid vector as the vector; an antibiotic-resistant gene as the marker gene; and a *Bacillus* bacterium, a *Rodococcus* bacterium, or a *Gordonia* bacterium as the host cells for introducing the DNA tag is exemplified. If the DNA tag is introduced in such combination, the DNA tag can be stably introduced into the genome.

The host cells including the vector introduced are cultured depending on the type of the cells. In this case, cells including the vector introduced by a marker gene are selected. For example, in the case where transformation is performed using a vector including an antibiotic-resistant marker gene integrated, an antibiotic suitable for a medium is added, and survival cells are selected.

In the step (iii), the cells transformed in the step (ii) are appropriately cultured so that the generation number increases (continuous culture) or subcultured in a medium containing no medicament such as an antibiotic, to thereby obtain a mutant in which the DNA tag has been subjected to homologous recombination.

Further, in the case where a gene encoding a fluorescent protein is used as the marker gene, a solution obtained by diluting a culture medium is plated in an appropriate agar medium or the like so that single colonies can be obtained, and UV irradiation may be performed to select colonies showing fluorescence. In the case of a gene encoding an enzyme which catalyzes a coloring reaction, as appropriate, a culture medium is plated in an appropriate agar medium or the like containing a substrate for the coloring reaction in the same way as above, and colonies can be selected by the coloring reaction. Even if another marker gene is used, a conventionally known detection method can be appropriately employed depending on the type of the marker gene used.

Figure 8:
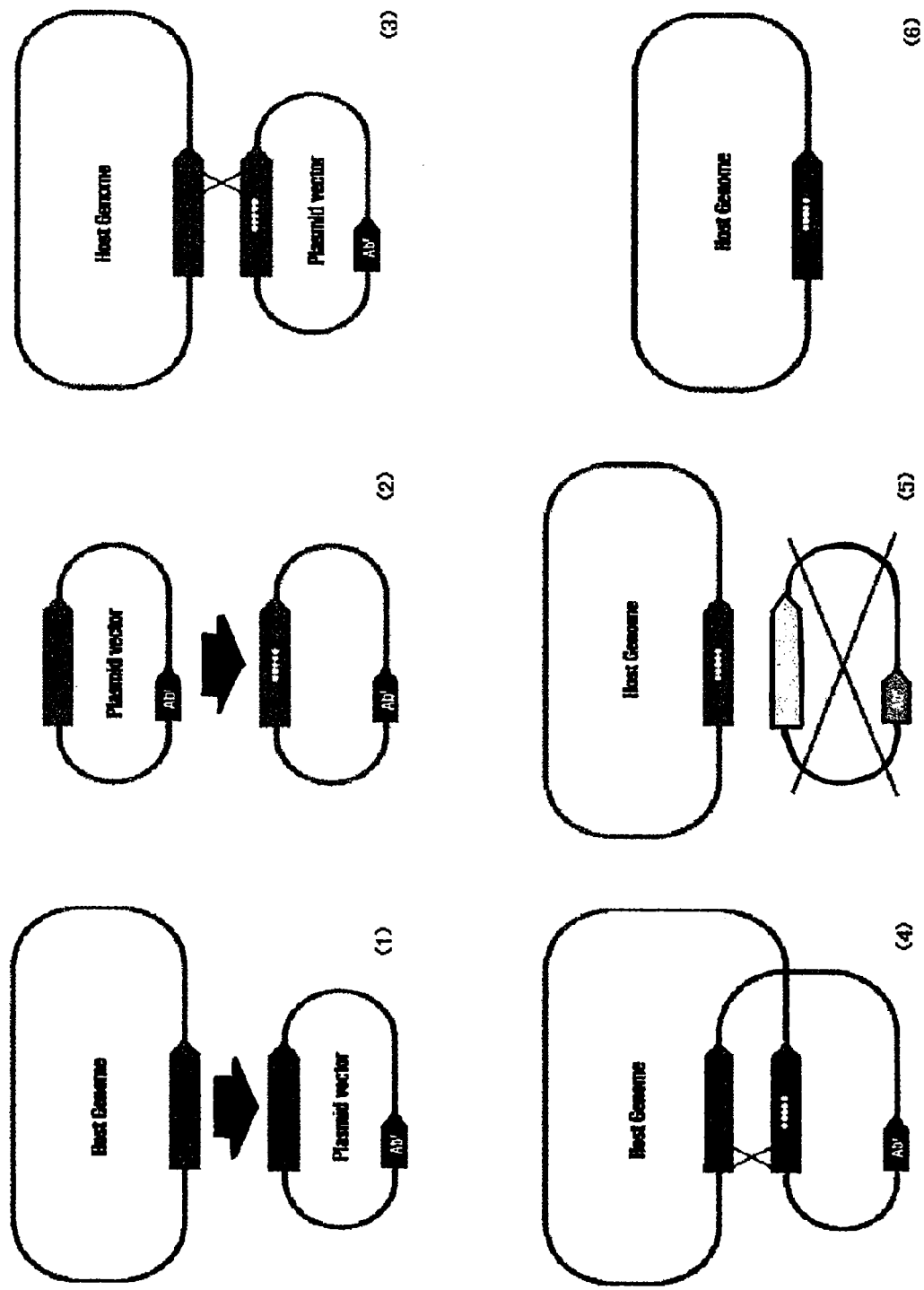
FIG. 8 is a scheme illustrating examples of a method of introducing a DNA tag. In the item (1) of this figure, DNA including a base sequence corresponding to a first coding sequence is cloned into a vector including an antibiotic-resistant marker for a host organism. In the item (2), a point mutation is introduced into DNA including a base sequence corresponding to the first coding sequence cloned. In the item (3), the vector is introduced into the host, and selection is performed using an antibiotic (in this procedure, a mutant produced by homologous recombination is obtained). In the item (4), the thus obtained mutant is cultured in a medium containing no antibiotic. In the item (5), a mutant which has lost its antibiotic resistance by the homologous recombination is obtained. In the item (6), a mutant which includes the DNA tag introduced properly and has no vector sequence is obtained by sequencing.

The cells including the DNA tag introduced are appropriately cultured depending on the type of the cells. In this procedure, the culture is repeated 10 to 100 times, preferably 30 to 100 times. In this procedure, subculture may be performed. As mentioned above, when the generation number increases for a long period of time to culture the cells, the marker gene and vector sequence may be removed by single crossover, to thereby obtain a mutant of interest where only the DNA tag has been subjected to homologous substitution. In this case, in the homologous regions added to the upstream and downstream of the DNA tag sequence, it is impossible to guess the region where the single crossover occurs (the former region or latter region). However, bacterial strains in which the single crossover occurs in opposite positions of the single crossover in the mutants obtained in the step (ii) are mutants of interest, and hence 50% of the mutants are desired strains. The desired strains can be easily obtained by screening using a procedure such as colony PCR using the DNA tags introduced as primers or by colony PCR using primers designed in the vector. In a final step, sequencing may be performed to confirm whether introduction of the DNA tag into regions to be treated is performed properly. The flow of the method is illustrated in FIG. 8.

As a method of storing mutant cells, an appropriate method may be selected from conventionally known methods of storing cells in consideration of the type of the cells and preservation period. Examples of the method include refrigerated storage, frozen storage, freeze-dry storage, and slant storage. Meanwhile, in the case where cells including the DNA tag introduced are preserved for several tens of years, it is particularly preferred to use a microorganism having an ability to form spores as host cells and store the cells in spore states.

To confirm that the DNA tag is introduced properly by homologous substitution in a mutation introduction region of the mutant including the DNA tag introduced, obtained by the above-mentioned steps and whether a vector sequence does not remain in the genome, sequencing may be performed in accordance with a conventionally known method. The present invention includes the thus obtained mutant including the DNA tag introduced.

The above-mentioned descriptions show the procedures using homologous recombination by the single crossover, but the method of manufacturing the mutant including the DNA tag introduced of the present invention is not limited thereto and includes a variety of procedures based on the procedure. For example, in the step (i), a DNA tag region is cloned using a vector including replication-competent on in an organism into which the DNA tag is introduced, and in the step (ii), a mutant in which homologous recombination has been performed by double crossover is obtained. For example, a mutant of interest can be obtained by PCR using a primer including the DNA tag sequence and a primer designed on a further upstream in the upstream region of the DNA tag sequence cloned into the vector in the genomic DNA sequence of the host. In the step (iii), the bacterium is appropriately cultured in a medium containing no antibiotic used as the marker, to thereby obtain a mutant in which the plasmid has been removed. As mentioned above, a variety of introduction methods can be performed with ingenuities in the respective steps, but the procedure of the homologous recombination by the single crossover is simple and accurate.

(3) Monitoring Method Using DNA Tag

The present invention provides a method of monitoring the cells into which the DNA tag has been introduced in the section (2) described above using the primer that recognizes the DNA tag designed in the section (1) described above. According to this method, it is possible to accurately grasp progress of cleanup and dispersion of microorganisms using the DNA tag as an indicator. For example, in the case where microorganisms including the DNA tag introduced are used for bioremediation, environmental genomic DNAs (whole DNA obtained from natural environment) are obtained from an environment where the microorganisms may be spread, and the microorganisms may be detected and quantified by quantitative PCR using a primer which recognize the DNA tag.

More specifically, microorganisms including the DNA tag in their genome are spread to perform bioremediation, and the number of cells of the microorganism is appropriately quantified with time. Then, depending on the increase or decrease in the number of the cells, additional spread of the microorganisms may be appropriately performed. Meanwhile, for example, at the time when soil improvement is completed, soil or water is collected in a region excluding the spread region and, if the microorganisms are not detected, it is possible to judge that the microorganisms are not dispersed to the outside.

(4) Method of Labeling Organism

The present invention provides a method of labeling an organism, which includes introducing a base sequence obtained based on the above-mentioned method of determining the DNA tag and introduction site into a predetermined site in genomic DNA of the organism. The method of obtaining the DNA tag and the method of determining the introduction site and the method of introducing the DNA tag into the genomic DNA of the organism are as described above.

EXAMPLES

Hereinafter, the present invention is described in more detail by way of test examples and the like. However, the present invention is not limited thereto.

Reference Test Example 1

Using data of the whole genomic sequences of bacteria, archaea, and viruses registered in the NCBI, base sequences which are less likely to be used in the living world (1 to 12 bases) were obtained using a program P1 (hereinafter, may be abbreviated as "specific sequences"). In a search of the base sequences which are less likely to be used, the maximum length of each sequence was set to 12 bases from the viewpoint of the computation time. Therefore, if the computation time is not considered, further longer sequences may be obtained.

Trial (a): From data of genomic sequence of *Rhodococcus* sp. to be used for bioremediation, 15 to 30 bases (base sequences having lengths which may be used as primers for quantitative PCR) were obtained at random and aligned for environmental metagenome data currently registered in the NCBI, and the probability of the appearance of each of the sequences in the environmental metagenome was calculated (the trial was repeated ten thousand times).

Trial (b): From the data of the genomic sequence of *Rhodococcus* sp., 15 to 30 bases were obtained at random, and a data set was prepared by adding silent mutations at random to the third bases in codons of the base sequences. The sequences were aligned for environmental metagenome data currently registered in the NCBI, and the probability of the appearance of each of the sequences in the environmental metagenome was calculated (the trial was performed ten thousand times).

Trial (c): From the data of the genomic sequence of *Rhodococcus* sp., 15 to 30 bases were obtained at random, and a data set including a 12-base specific sequence incorporated into a region was prepared by adding silent mutations to the third bases in codons of the base sequences to search the region that was able to be designed so as to contain the specific sequence. The sequences were aligned for environmental metagenome data currently registered in the NCBI, and the probability of the appearance of each of the sequences in the environmental metagenome was calculated (the trial was performed one thousand times).

[Results]

Figure 6:
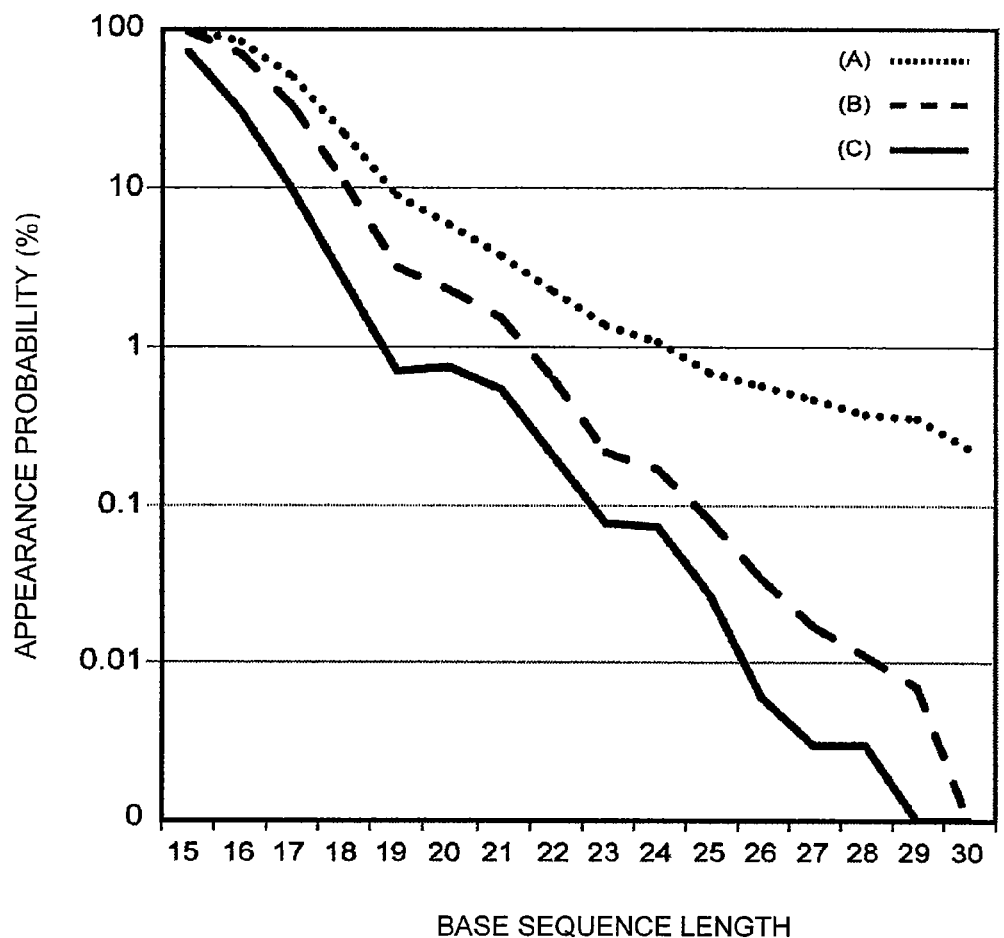
FIG. 6 is a graph illustrating lengths of bases and probability of occurrence thereof in a metagenome (the vertical axis has a logarithmic scale) in the respective trials.

The base lengths and appearance ratios in metagenomes in each of the trials (a) to (c) are illustrated in FIG. 6. In general, the maximum length of a primer is about 30 bases. FIG. 6 illustrates that the primer having a base sequence having a base length of 29 or 30 bases did not appear at all in the environmental metagenome in each of the trials (b) and (c) as the appearance ratio is zero for the primer. That is, the results have shown that, in the case where primers are designed using the method of the present invention, the probability of non-specific binding of the primers to genome sequences in the environment can be drastically reduced in a range of primers having lengths usually designed as compared to the case where the primers are designed at random.

Test Example I

1. Procedure and Target (1-1) Determination of Type of Target Organism

As a target organism, *Bacillus subtilis* strain 168 (*Bacillus subtilis*) was selected. Some of *Bacillus* bacteria have an ability to degrade petroleum and are widely used in the field of bioremediation. Therefore, *Bacillus subtilis*, whose whole genome sequence had been determined and many of whose essential genes had been identified, was considered to be suitable as a model organism of this analysis.

(1-2) Determination of Target Gene

Information of base sequences of a total of 4,106 protein coding genes of *Bacillus subtilis* was obtained from GenBank (worldwide web at ncbi.nlm.nih.gov/) of NCBI. Subsequently, 270 essential genes (Kobayashi et al. Proc. Natl. Acad. Sci. USA. 003 Apr. 15; 100(8): 4678-83.) were removed from the genes.

Meanwhile, the whole genome sequence information of the organism where a tag is to be introduced is not always obtained. If not, DNA sequences on the periphery of 16S rRNA gene may be appropriately determined using universal primers to introduce the tag. To verify that primers with sufficiently high specificity can be designed even in such case, only peripheral genes of rRNA gene were used in this analysis. Specifically, only genes located in positions within 10 kbp of the periphery of the rRNA gene (5 kbp from the 5'-end of rRNA gene toward the 5' direction, 5 kbp from the 3'-end toward the 3' direction) were selected as genes where the tag was to be introduced in this analysis, and the other genes were eliminated. As a result, 93 genes (a total of about 70,000 bp) were selected as targets of this analysis.

(1-3) Preparation of Fragmented Sequences

The 93 genes thus determined were each fragmented into a window size having 18 bases to prepare 67,953 fragmented sequences.

(1-4) Preparation of Negative Control Data

To examine the appropriateness of the present invention, fragmented sequence including no DNA tag introduced by a silent mutation was used as a control. From the 67,953 fragmented sequences determined by the procedure (1-3), a total of 2,238 candidates, which were judged to have sufficient functions as primer sequences based on the following function evaluation criteria (a) to (c), were selected as controls (hereinafter, referred to as negative control data). It should be noted that all the following criteria (a) to (c) are usually used for design of primers.

(a) Having a GC content of 40% or more and 60% or less.

(b) Having a Tm value of 55° C. or more and 65° C. or less.

(c) Having terminal bases of G or C.

(1-5) Preparation of DNA Tag-Introduced Sequence

Each of the 67,953 fragmented sequences was subjected to silent mutations to prepare all patterns of sequences different from the original sequences. Moreover, after the silent mutations, functions of the sequences as primer sequences were evaluated based on the above-mentioned function evaluation criteria (a) to (c), and candidates were screened. As a result, 812,864 tag-introduced sequences were prepared.

(1-6) Calculation of Nearest Match Score (Nms) and Appearance Frequency of DNA Tag-Introduced Sequence The 812,864 DNA tag-introduced sequences were used as query sequences, and homology searches were performed for the whole genome database to calculate NMSs and appearance frequency. The whole genome database includes the genome base sequences of all prokaryotes, archaea, plasmids, and viruses the whole genome sequence of each of which has been determined. All the data of the genome base sequences were obtained from the FTP site of the NCBI (worldwide web at ncbi.nlm.nih.gov/) (Table 1). In the homology searches, NCBI Blast (blast.ncbi.nlm.nih.gov/Blast.cgi) was used. It should be noted that, in this analysis, regions each having less than 50% homology were not counted as homologous regions.

TABLE 1

Contents of whole genome database

| Type of genome | Target | Total file number | Total base number (bp) |
|---|---|---|---|
| Complete genome | Bacteria | 714 | 2,269,972,014 |
| | Archaea | 55 | 113,127,648 |
| | Plasmid | 501 | 67,408,122 |
| | Viruses | 3,173 | 61,226,978 |

2. Control Experiment (2-1) To examine the appropriateness of the present invention, first, the following sequences (w) to (z) were prepared.

(w) A total of 234 all tag-introduced sequences each having an NMS of less than 50%.

The sequences correspond to about 0.025% from the bottom of NMS rank of all the 812,864 tag-introduced sequences prepared in the procedure (1-6).

(x) 404 sequences corresponding to about 0.05% from the bottom of NMS rank of all the 812,864 tag-introduced sequences prepared in the procedure (1-6).

(y) 409 tag-introduced sequences corresponding to about 0.05% from the top of NMS rank of all the 812,864 tag-introduced sequences prepared in the procedure (1-6).

(z) 2,238 tag-unintroduced sequences (negative control data created in the procedure (1-4)).

(2-2) Subsequently, to virtually imitate an environment where a large indefinite number of DNA sequences were present as soil or the like used as a target of bioremediation, environmental metagenome sequences registered in the NCBI were obtained and provided as an environmental DNA database (Table 2).

TABLE 2

Contents of environmental DNA database

| Type of genome | Target | Total file number | Total base number (bp) |
|---|---|---|---|
| Environmental genome | coral | 15 | 101,879,793 |
| | Fish | 8 | 49,317,878 |
| | Fossil | 2 | 53,822,347 |
| | Freshwater | 8 | 102,870,126 |
| | Human gut | 13 | 462,989,954 |
| | Human lung | 2 | 10,818,592 |
| | Marine | 15 | 4,948,763,548 |
| | Microbial mat | 10 | 84,253,870 |
| | Mine drainage | 3 | 70,335,918 |
| | Mosquito | 3 | 164,887,115 |
| | Mouse gut | 6 | 53,922,645 |
| | Saltern | 18 | 148,587,256 |
| | Soil | 1 | 612,702 |
| | Stromatolite | 6 | 154,900,267 |
| | Termite gut | 1 | 55,038,603 |
| | Others | 10 | 357,259,566 |

Figure 7:
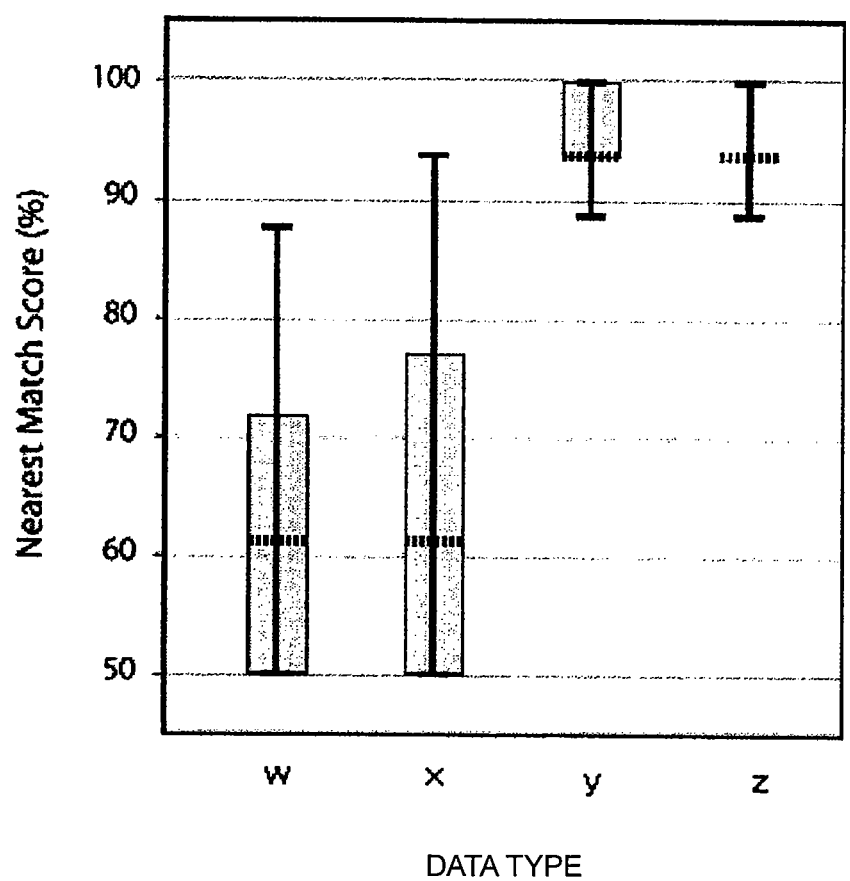
FIG. 7 is a boxplot illustrating results of a homology search of the respective data sets on an environmental DNA database. In this figure, the dotted lines show mean values, the both ends of the lines show the maximum values and minimum values, and the both ends of the boxes represent the first quartiles and third quartiles.

A homologous search using Blast as an environmental DNA database was performed using the sequences (w) to (z) as query sequences, to thereby calculate NMS for each sequence. The distribution of the NMSs in the respective data sets (w) to (z) is illustrated by a boxplot (FIG. 7).

Comparison of w, x, and y indicates that, as the NMSs and appearance frequency calculated based on the whole genome database become lower, the number of homologous regions that appear in the environmental DNA database becomes smaller. This indicates that DNA of an organism includes a sequence which is universally hardly appears or universally easily appears and means that the specificity of primers in the environmental DNA can be estimated to a certain degree on the basis of NMSs used as indices calculated from restricted genome sequences (in this analyses, the whole genome database).

Next, it is found that the sequences (w and x) having low NMSs and appearance frequency in the whole genome database have a small number of homologous regions in the environmental DNA database as compared to the original sequences (z) where no DNA tag was introduced. This result indicates the appropriateness of the present invention, that is, the fact that the specificity of the primers can be improved by inserting the silent mutations so that the NMSs are lowered.

The dataset (z) shows similar values in the first quartiles, third quartiles, and medians. It should be noted that, in this analysis, regions each having less than 50% homology were not counted, and hence all the NMSs in sequences where NMS=0 was calculated were defined as 50. Parameters of w, x, y, and Z are 234, 404, 409, and 2,238, respectively.

In general, primers each having about 80% sequence homology are known to cause nonspecific reactions. FIG. 7 reveals that all the sequences (z) where no DNA tag was inserted each have a region having 80% or more homology in the environmental DNA database. This means that there is no region in which a specific primer can be designed on the 93 genes selected from *Bacillus subtilis* unless the DNA tag technology is used. On the other hand, the figure reveals that 75% or more of the sequences (w or x) including the DNA tag inserted so as to reduce NMSs have specificity as primers even in the environmental DNAs (calculated from the third quartiles in the following boxplot).

Test Example II

To obtain a mutant which is not included in the "recombinant organisms" specified by the Cartagena Law and includes the DNA tag introduced, the following test was performed.

(II-1) Determination of Target Organism and Region where DNA Tag is Introduced, and Preparation of Vector for Transformation In bioremediation, a variety of microorganisms capable of performing environmental cleanup is used in open environments, and hence only organisms which are not included in the "recombinant organisms" specified by the Cartagena Law can be used industrially. For example, in the case where cleanup of soil polluted with petroleum is performed, *Bacillus* bacteria are generally used. Therefore, *Bacillus subtilis* strain 168 was used in the test.

Figure 9:
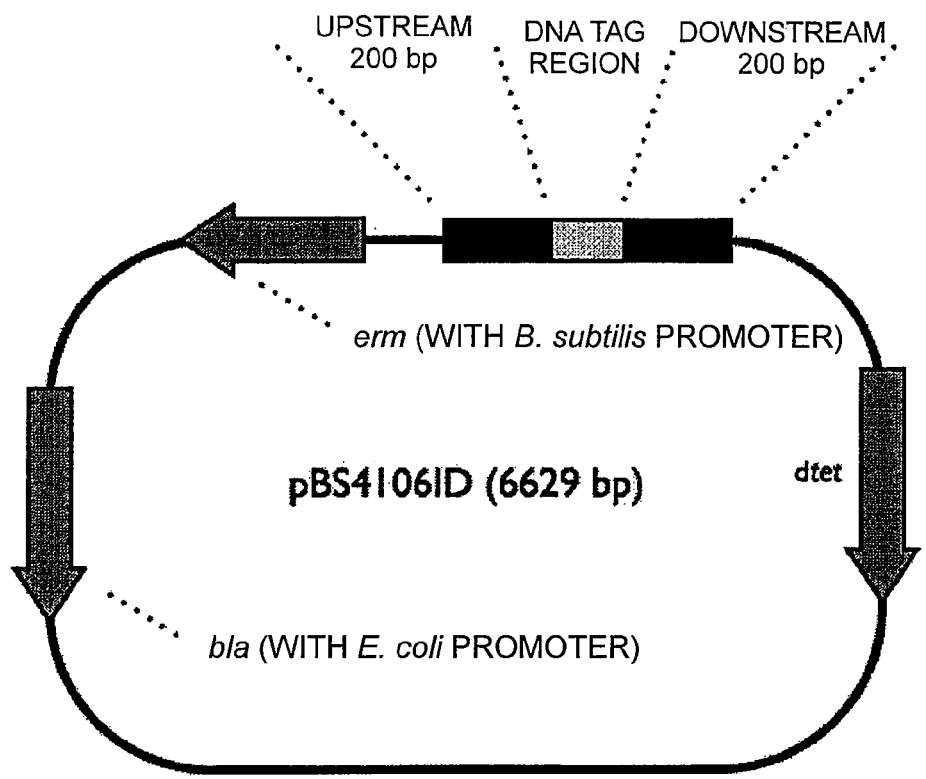
FIG. 9 is a schematic diagram illustrating pBS4106ID constructed in Reference Test Example 3.
Figure 11:
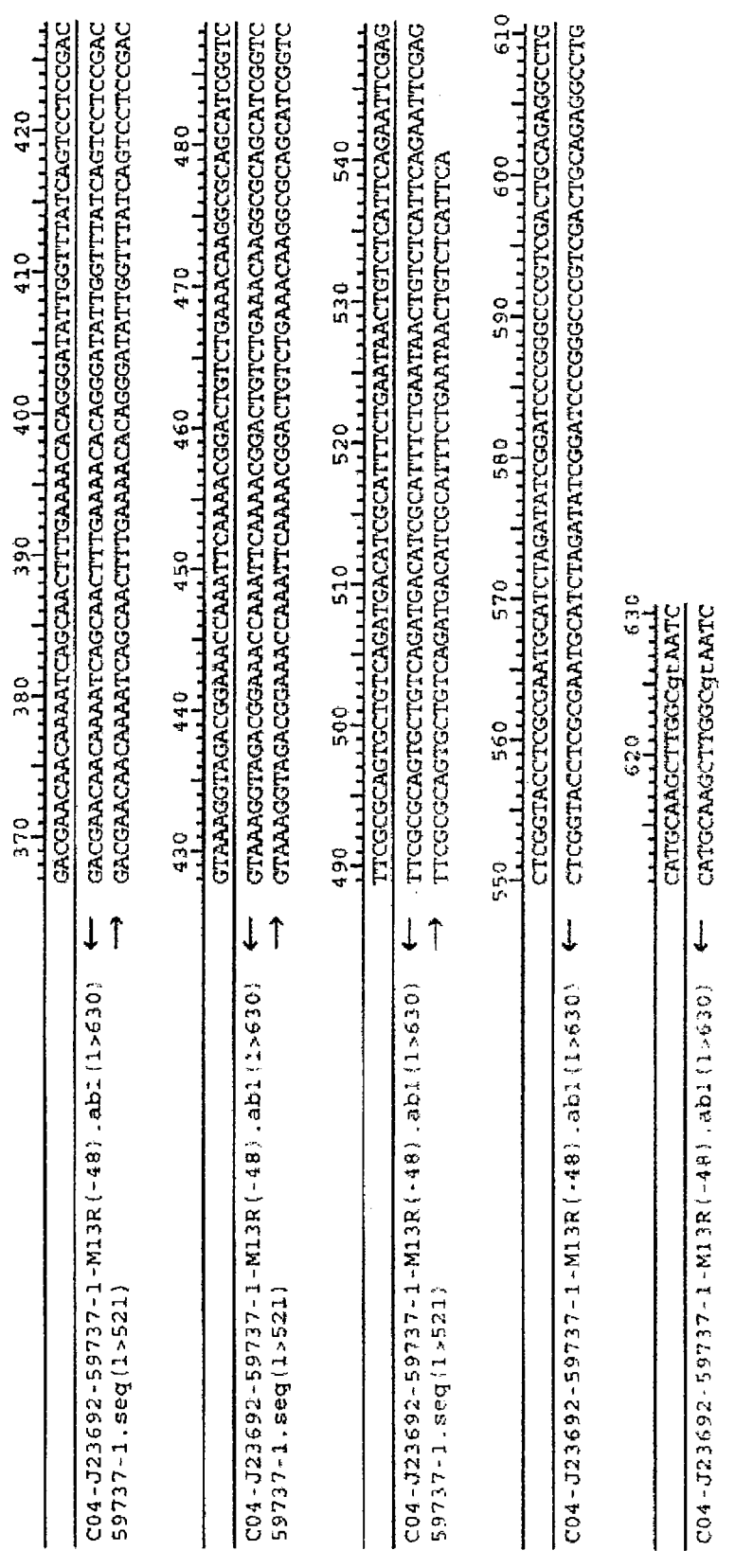

As a target gene into which the DNA tag was to be introduced, a gene which was considered to have little influence on proliferation of host cells was selected. The gene is a gene having a locus tag of BSU03680, a gene locus of 417561-419315, and unknown functions. Before a test of insertion of the DNA tag into the gene, a region of 418431-418547, which corresponds to an intermediate region of the gene, was defined as a region into which the DNA tag was to be introduced, and a sequence including a random silent mutation introduced was defined as a pseudo DNA tag. An artificial gene having a full length of 520 bases, obtained by adding the upstream sequence of 200 bases of the sequence and the downstream sequence of 200 bases of the sequence, was synthesized by a known method of constructing an artificial gene (GenScript), and the gene was constructed on a plasmid vector pHASH203 using an EcoRI restriction enzyme site added on the upstream and downstream and was named pBS4106ID (FIG. 9). As a resistant gene, an erythromycin-resistant gene was used. Further, the plasmid was constructed using *Escherichia coli* DH5α. The results of sequencing are shown in FIGS. 10 and 11.

Shown below are the sequence of the region into which the DNA tag is introduced (SEQ ID NO: 1), the DNA tag (SEQ ID NO: 2), and the sequence after introduction of the DNA tag (SEQ ID NO: 3). It should be noted that, in SEQ ID NO: 2, the shaded parts each show that a silent mutation has been introduced.

TABLE 3

5'-CCTGAAGACGCGGCGGCTGCGCCAAGAGTCGGGATAACCGGACTCG

GTGTATCACAAGGAAAAGAGACCAGTGATGCAGTGATCGCTGGCAACCT

CATTACCGGATTTTCAACTGGA-3' (SEQ ID NO: 1)

TABLE 4

CCCGAAGATGCGGCAGCCGCCCCTAGAGTCGGTATAACTGGACTGGGAGTGTCACAAGGCAAGGAAACCAGTGACGCAG

TGATTGCAGGCAACCTCATAACCGGCTTCTCTACAGGG

-3' (SEQ ID NO: 2)

Shown below is the gene sequence including the DNA tag introduced. The DNA tag regions are surrounded by squares (including about 200 bases in each of the upstream and the downstream).

TABLE 5

5'-
AAGGATATGGCGAAGGTGACGTTGATTATGAGGAACCGATTAATGTATCAATTCGCAATAACCACTTTGTTGGAAACGTT

TCAAGTTCTGTGACCAATTTTAACGGGTATGGCATTTTAATAGAAGGAAATCACTCAGACAATACAATCAGCTACGGATA

TGGGACGCAAACAGTGATCAAGGGCAATATTCTGAGACGC CCCGAAGATGCGGCAGCCGCCCCTAGAGTCGGTATAACT

GGACTGGGAGTGTCACAAGGCAAGGAAACCAGTGACGCAGTGATTGCAGGCAACCTCATAACCGGCTTCTCTACAGGGA

TABLE 5-continued

```
TTGATGTCAGGGGAAAGAGCGTTCTTGTGACGAACAACAAAATCAGCAACTTTGAAAACACAGGGATATTGGTTTATCAG

TCCTCCGACGTAAAGGTAGACGGAAACCAAATTCAAAACGGACTGTCTGAAACAAGGCGCAGCATCGGTCTTCGCGCAGT

GCTGTCAGATGACATCGCATTTCTGAATAACTGTCTCATTCA
```

-3' (SEQ ID NO: 3)

(II-2) Transformation of *B. subtilis* Strain 168

*B. subtilis* strain 168 was transformed with pBS4106ID. First, as preculture, *B. subtilis* strain 168 was inoculated into any LB agar medium (Tripton 10 g/L, Yeast Extract 5 g/L, NaCl 10 g/L, 1.5% agarose) using a platinum needle and cultured at room temperature. Next, a single colony was inoculated into 5 mL of a CI medium (1×MM medium 5 mL, 50% glucose 50 µL, 1M MgSO4 25 µL, L-leucine 5 mg/mL 50 µL, L-tryptophan 5 mg/mL 50 µL, 5% Yeast Extract 50 µL) so that OD660 was 0.1 and cultured with shaking at 37° C. When OD660 reached 1.5, 500 µL of the culture solution was separated in a centrifugal tube and centrifuged at 15,000 rpm for 2 minutes, and the supernatant was removed, to thereby obtain a bacterial cell pellet.

The bacterial cell pellet was suspended in 1 mL of a CII medium (1×MM medium 5 mL, 50% glucose 50 µL, 1M MgSO4 25 µL, L-leucine 5 mg/mL 5 µL, L-tryptophan 5 mg/mL 5 µL, 5% Yeast Extract 25 µL) using Vortex, and 100 µL of the suspension was dispensed in a small test tube. Thereafter, 100 ng of a vector was added, and the bacteria were cultured with shaking at 37° C. for 90 minutes. After culture, 300 µL of an LB medium was added, and the bacteria were further cultured for 60 minutes, plated in an LB agar medium containing 5 µg/ml erythromycin, and cultured at 37° C. overnight. In all resultant colonies, a sequence of pBS4106ID was introduced into the genome of the host by homologous recombination (single crossover). The transformant of *B. subtilis* strain 168 thus obtained was named strain BS4106A.

(III-3) Acquirement of Mutant of Interest

To remove extra sequences derived from the vector pBS4106ID by exchanging only the DNA tag regions for gene regions in the genome of the host, strain BS4106A was inoculated into 5 mL of an LB medium containing no reagent (erythromycin) and cultured with shaking at 37° C. for 36 hours (if the bacteria was divided once per 30 minutes, about 70th generation of the bacteria was obtained). The culture solution was diluted 1000-fold with an LB medium and plated in an LB agar medium. The resultant colonies were patched on each of an LB agar medium containing 5 µg/ml erythromycin and an LB agar medium containing no reagent using a platinum needle, to thereby obtain an erythromycin-sensitive strain. For 200 colonies of the bacterial strain thus obtained, primers (SEQ ID NOS: 4 and 5) were designed from an inner sequence of pBS4106ID, and colony PCR was performed. A bacterial strain which was not amplified by the colony PCR were subjected to sequencing, to thereby obtain a bacterial strain including the DNA tag introduced properly. The bacterial strain thus obtained was named BS4106ID. It should be noted that, in strain BS4106ID, only the DNA tag regions were exchanged for the gene regions in the genome of the host, and hence the strain was not included in the "recombinant organisms" specified by the Cartagena Law.

Primer sequences used in the colony PCR are as follows.

```
ERM-F
                                       (SEQ ID NO: 4)
5'-CGTAGAGCACACGGTTTAACG-3'

TET-R2
                                       (SEQ ID NO: 5)
5'-GCCATAGTGACTGGCGATGC-3'
```

Primer sequences used in the sequencing are as follows.

```
bs4106id_F
                                       (SEQ ID NO: 6)
5'-AGGATATGGCGAAGGTGACG-3' bs4106id_R
                                       (SEQ ID NO: 7)
5'-GTCATCTGACAGCACTGCGC-3'
```

REFERENCE SIGNS LIST

1 computer
2 display unit
3 operation unit
4 network
5 database (DB)
11 computer processing unit (CPU)
12 rewritable memory (RAM)
13 recording unit
14 interface unit (IF unit)
15 internal bus

SEQUENCE LISTING FREE TEXT

SEQ ID NO: 2 represents a DNA tag to be introduced.
SEQ ID NO: 3 represents a gene locus 417561-419315 of *Bacillus subtilis* strain 168 including the DNA tag introduced.
SEQ ID NO: 4 represents an ERM-F primer.
SEQ ID NO: 5 represents a TET-R2 primer.
SEQ ID NO: 6 represents a bs4106id_F primer.
SEQ ID NO: 7 represents a bs4106id_R primer.
SEQ ID NO. 8 represents an example of amino acid encoded by CDS.
SEQ ID NO. 9 represents an example of a CDS sequence.
SEQ ID NO. 10 represents an example of a fragmented CDS sequence.
SEQ ID NO. 11 represents an example of a fragmented CDS sequence.
SEQ ID NO. 12 represents an example of a fragmented CDS sequence.
SEQ ID NO. 13 represents an example of a fragmented CDS sequence.
SEQ ID NO. 14 represents an example of a fragmented CDS sequence.

SEQ ID NO. 15 represents an example of the silent mutated CDS sequence.
SEQ ID NO. 16 represents an example of the homologous region to the silent mutated CDS sequence.
SEQ ID NO. 17 represents an example of the homologous region to the silent mutated CDS sequence.
SEQ ID NO. 18 represents the partial sequence of pBS4106ID.
SEQ ID NO. 19 represents an example of the silent mutated CDS sequence.
SEQ ID NO. 20 represents an example of the silent mutated CDS sequence.
SEQ ID NO. 21 represents an example of the silent mutated CDS sequence.
SEQ ID NO. 22 represents an example of the silent mutated CDS sequence.

The invention claimed is:

1. A method of determining a DNA tag which is a base sequence to be introduced into a genomic DNA sequence of an organism and an introduction site of the DNA tag into the genomic DNA sequence, the method comprising
  (A) a processing unit of a computer performing the following steps S1 to S8:
  a step S1 of obtaining a protein coding sequence from the genomic DNA sequence;
  a step S2 of determining a region within the protein coding sequence obtained in step S1 that has no influence on a biological function of the organism even if the sequence is subjected to a silent mutation, as a first coding sequence;
  a step S3 of obtaining a plurality of second coding sequences each including a partial sequence in the first coding sequence and having a predetermined length and recording sites of the second coding sequences in the protein coding sequence;
  a step S4 of obtaining one or more third coding sequences produced by subjecting the corresponding second coding sequences obtained in the step S3 to a silent mutation;
  a step S5 of judging whether or not each of the third coding sequences obtained in step S4 satisfy a predetermined condition and determining one or more sequences among the third coding sequences judged to satisfy the predetermined condition as fourth coding sequences;
  a step S6 of performing a homology search for each of the fourth coding sequences;
  a step S7 of determining an NMS for each of the fourth coding sequences using the results of the homology search performed in step S6; and
  a step S8 of determining the fourth coding sequence corresponding to the NMS with the minimum value among the NMSs determined for each of the fourth coding sequences in step S7 as the DNA tag, and determining the site of the second coding sequence corresponding to the fourth coding sequence determined as the DNA tag, as the introduction site, wherein:
  the predetermined condition comprises a condition where a polynucleotide including the third coding sequence or a complementary base sequence thereof is suitable as a primer; and
  the NMS indicates a degree of homology; and
  (B) recording the determined DNA tag and the introduction site to a recording unit.

2. A method of determining a DNA tag and an introduction site according to claim 1, further comprising,
  determining an appearance frequency for each of the fourth coding sequences in step S7, the appearance frequency indicating the number of genomes that a region homologous to the fourth coding sequence is detected by the homology search performed in step S6, and when a plurality of fourth coding sequences corresponding to the NMS with the minimum value exists in step S8,
  a step S9 of determining the fourth coding sequence corresponding to the appearance frequency with the minimum value among the appearance frequency of the plurality of fourth coding sequences corresponding to the NMS of the minimum value as the DNA tag, and determining as the introduction site, the site of the second coding sequence corresponding to the fourth coding sequence determined as the DNA tag.

3. A method of determining a DNA tag and an introduction site according to claim 1, wherein the condition where a polynucleotide including the third coding sequence or a complementary base sequence thereof is suitable as a primer comprises the following:
  the complementary base sequence has a CG content of 45 to 55%;
  the complementary base sequence has a $T_m$ value of 55 to 65° C.; and
  the complementary base sequence is free of four or more consecutive identical bases.

4. A method of manufacturing a DNA-tag-introduced mutant, the method comprising the following steps:
  (i) preparing the DNA tag determined by the method according to claim 1 and cloning the DNA tag into a vector including a marker gene;
  (ii) transforming a cell of an organism with the vector having the DNA tag cloned in the step (i); and
  (iii) removing the marker gene by continuous culture or subculture of the cell transformed in the step (ii) and obtaining a mutant having the DNA tag introduced into a genome through homologous recombination.

5. A method according to claim 4, further comprising the step of confirming that the marker gene is absent in the genome of the organism.

6. A method of labeling an organism, the method comprising
  (i) preparing the DNA tag determined by the method according to claim 1 and
  (ii) introducing the DNA tag into the introduction site of the genomic DNA of the organism, the introduction site determined by the method according to claim 1, using a vector having the DNA tag cloned thereinto.

7. A method of manufacturing a vector, the method comprising
  (i) preparing the DNA tag determined by the method according to claim 1 and
  (ii) cloning the DNA tag into a vector including a marker gene.

8. A computer readable medium encoded with a computer program for allowing a processing unit of a computer to execute a function for determining a DNA tag which is a base sequence to be introduced into a genomic DNA sequence of an organism and an introduction site of the DNA tag into the genomic DNA sequence, the encoded program allows the processing unit of the computer to execute:
- a first function for obtaining a protein coding sequence from the genomic DNA sequence;
- a second function for determining a region within the protein coding sequence obtained by the first function that has no influence on a biological function of the organism even if the sequence is subjected to a silent mutation, as a first coding sequence;
- a third function for obtaining a plurality of second coding sequences each including a partial sequence in the first coding sequence and having a predetermined length and recording sites of the second coding sequences in the protein coding sequence;
- a fourth function for obtaining one or more third coding sequences produced by subjecting the corresponding second coding sequences obtained in the third function to a silent mutation;
- a fifth function for judging whether or not each of the third coding sequences obtained by the fourth function satisfy a predetermined condition and determining one or more sequences among the third coding sequences judged to satisfy the predetermined condition as fourth coding sequences;
- a sixth function for performing a homology search for each of the fourth coding sequences;
- a seventh function for determining an NMS for each of the fourth coding sequences using the results of the homology search performed by the sixth function; and
- an eighth function for determining the fourth coding sequence corresponding to the NMS with a minimum value among the NMSs determined for each of the fourth coding sequence in the seventh function as the DNA tag and determining the site of the second coding sequence corresponding to the fourth coding sequence determined as the DNA tag as the introduction site, wherein the predetermined condition comprises a condition where a polynucleotide including the third coding sequence or a complementary base sequence thereof is suitable as a primer; and the NMS indicates a degree of homology.

* * * * *

SEQUENCE LISTING

```
<160> NUMBER OF SEQ ID NOS: 22

<210> SEQ ID NO 1
<211> LENGTH: 117
<212> TYPE: DNA
<213> ORGANISM: Bacillus subtilis

<400> SEQUENCE: 1
cctgaagacg cggcggctgc gccaagagtc gggataaccg gactcggtgt atcacaagga      60
aaagagacca gtgatgcagt gatcgctggc aacctcatta ccggattttc aactgga       117

<210> SEQ ID NO 2
<211> LENGTH: 117
<212> TYPE: DNA
<213> ORGANISM: artificial sequence
<220> FEATURE:
<223> OTHER INFORMATION: nucleotide sequence of DNA tag

<400> SEQUENCE: 2
cccgaagatg cggcagccgc ccctagagtc ggtataactg gactgggagt gtcacaaggc      60
aaggaaacca gtgacgcagt gattgcaggc aacctcataa ccggcttctc tacaggg       117

<210> SEQ ID NO 3
<211> LENGTH: 520
<212> TYPE: DNA
<213> ORGANISM: artificial sequence
<220> FEATURE:
<223> OTHER INFORMATION: DNA sequence including DNA tag

<400> SEQUENCE: 3
aaggatatgg cgaaggtgac gttgattatg aggaaccgat taatgtatca attcgcaata      60
accactttgt tggaaacgtt tcaagttctg tgaccaattt taacgggtat ggcattttaa     120
tagaaggaaa tcactcagac aatacaatca gctacggata tgggacgcaa acagtgatca     180
agggcaatat tctgagacgc cccgaagatg cggcagccgc ccctagagtc ggtataactg     240
gactgggagt gtcacaaggc aaggaaacca gtgacgcagt gattgcaggc aacctcataa     300
ccggcttctc tacagggatt gatgtcaggg gaaagagcgt tcttgtgacg aacaacaaaa     360
tcagcaactt tgaaaacaca gggatattgg tttatcagtc ctccgacgta aaggtagacg     420
gaaaccaaat tcaaaacgga ctgtctgaaa caaggcgcag catcggtctt cgcgcagtgc     480
tgtcagatga catcgcattt ctgaataact gtctcattca                          520

<210> SEQ ID NO 4
<211> LENGTH: 21
<212> TYPE: DNA
<213> ORGANISM: artificial sequence
<220> FEATURE:
<223> OTHER INFORMATION: ERM-F primer

<400> SEQUENCE: 4
cgtagagcac acggtttaac g                                               21
```

```
<210> SEQ ID NO 5
<211> LENGTH: 20
<212> TYPE: DNA
<213> ORGANISM: artificial sequence
<220> FEATURE:
<223> OTHER INFORMATION: TET-R2 primer

<400> SEQUENCE: 5
gccatagtga ctggcgatgc                                              20

<210> SEQ ID NO 6
<211> LENGTH: 20
<212> TYPE: DNA
<213> ORGANISM: artificial sequence
<220> FEATURE:
<223> OTHER INFORMATION: bs4106id_F primer

<400> SEQUENCE: 6
aggatatggc gaaggtgacg                                              20

<210> SEQ ID NO 7
<211> LENGTH: 20
<212> TYPE: DNA
<213> ORGANISM: artificial seqeunce
<220> FEATURE:
<223> OTHER INFORMATION: bs4106id_R primer

<400> SEQUENCE: 7
gtcatctgac agcactgcgc                                              20

<210> SEQ ID NO 8
<211> LENGTH: 22
<212> TYPE: PRT
<213> ORGANISM: Artificial Sequence
<220> FEATURE:
<223> OTHER INFORMATION: example of amino acid encoded by CDS

<400> SEQUENCE: 8

Ile Leu His Asp Tyr Ala Tyr Ser Pro Arg Ile Gly Leu Ala Pro Glu
1               5                   10                  15

Arg Cys Ser Thr Asp Ile
            20

<210> SEQ ID NO 9
<211> LENGTH: 66
<212> TYPE: DNA
<213> ORGANISM: Artificial Sequence
<220> FEATURE:
<223> OTHER INFORMATION: example of CDS

<400> SEQUENCE: 9
attctgcacg attacgctta tagtcctagg atcggattag cccccgaaag atgctccacc    60
gatata                                                              66

<210> SEQ ID NO 10
<211> LENGTH: 12
<212> TYPE: DNA
<213> ORGANISM: Artificial Sequence
<220> FEATURE:
<223> OTHER INFORMATION: example of fragmented CDS

<400> SEQUENCE: 10
attctgcacg at                                                       12
```

```
<210> SEQ ID NO 11
<211> LENGTH: 12
<212> TYPE: DNA
<213> ORGANISM: Artificial Sequence
<220> FEATURE:
<223> OTHER INFORMATION: example of fragmented CDS

<400> SEQUENCE: 11
ttctgcacga tt                                                         12

<210> SEQ ID NO 12
<211> LENGTH: 12
<212> TYPE: DNA
<213> ORGANISM: Artificial Sequence
<220> FEATURE:
<223> OTHER INFORMATION: example of fragmented CDS

<400> SEQUENCE: 12
tctgcacgat ta                                                         12

<210> SEQ ID NO 13
<211> LENGTH: 12
<212> TYPE: DNA
<213> ORGANISM: Artificial Sequence
<220> FEATURE:
<223> OTHER INFORMATION: example of fragmented CDS

<400> SEQUENCE: 13
ctgcacgatt ac                                                         12

<210> SEQ ID NO 14
<211> LENGTH: 12
<212> TYPE: DNA
<213> ORGANISM: Artificial Sequence
<220> FEATURE:
<223> OTHER INFORMATION: example of fragmented CDS

<400> SEQUENCE: 14
tgcacgatta cg                                                         12

<210> SEQ ID NO 15
<211> LENGTH: 12
<212> TYPE: DNA
<213> ORGANISM: Artificial Sequence
<220> FEATURE:
<223> OTHER INFORMATION: example of the silently mutated CDS

<400> SEQUENCE: 15
atcttacatg ac                                                         12

<210> SEQ ID NO 16
<211> LENGTH: 20
<212> TYPE: DNA
<213> ORGANISM: Artificial Sequence
<220> FEATURE:
<223> OTHER INFORMATION: example of homologous region to the silent
      mutated CDS (hit 1)

<400> SEQUENCE: 16
agttatctta gataaccagt                                                 20

<210> SEQ ID NO 17
<211> LENGTH: 20
<212> TYPE: DNA
<213> ORGANISM: Artificial Sequence
<220> FEATURE:
<223> OTHER INFORMATION: example of homologous region to the silent
      mutated CDS (hit 2)
```

```
<400> SEQUENCE: 17
cccaatcgta catctagcac                                                    20

<210> SEQ ID NO 18
<211> LENGTH: 630
<212> TYPE: DNA
<213> ORGANISM: Artificial Sequence
<220> FEATURE:
<223> OTHER INFORMATION: partial sequence of pBS4106ID

<400> SEQUENCE: 18
aaacgacggc cagtgaattc aaggatatgg cgaaggtgac gttgattatg aggaaccgat        60
taatgtatca attcgcaata accactttgt tggaaacgtt tcaagttctg tgaccaattt       120
taacgggtat ggcattttaa tagaaggaaa tcactcagac aatacaatca gctacggata       180
tgggacgcaa acagtgatca agggcaatat tctgagacgc cccgaagatg cggcagccgc       240
ccctagagtc ggtataactg gactgggagt gtcacaaggc aaggaaacca gtgacgcagt       300
gattgcaggc aacctcataa ccggcttctc tacagggatt gatgtcaggg gaaagagcgt       360
tcttgtgacg aacaacaaaa tcagcaactt tgaaaacaca gggatattgg tttatcagtc       420
ctccgacgta aaggtagacg gaaaccaaat tcaaaacgga ctgtctgaaa caaggcgcag       480
catcggtctt cgcgcagtgc tgtcagatga catcgcattt ctgaataact gtctcattca       540
gaattcgagc tcggtacctc gcgaatgcat ctagatatcg gatcccgggc ccgtcgactg       600
cagaggcctg catgcaagct tggcgtaatc                                       630

<210> SEQ ID NO 19
<211> LENGTH: 12
<212> TYPE: DNA
<213> ORGANISM: Artificial Sequence
<220> FEATURE:
<223> OTHER INFORMATION: example of the silently mutated CDS

<400> SEQUENCE: 19
atactccatg ac                                                            12

<210> SEQ ID NO 20
<211> LENGTH: 12
<212> TYPE: DNA
<213> ORGANISM: Artificial Sequence
<220> FEATURE:
<223> OTHER INFORMATION: example of the silently mutated CDS

<400> SEQUENCE: 20
atccatcatg ac                                                            12

<210> SEQ ID NO 21
<211> LENGTH: 12
<212> TYPE: DNA
<213> ORGANISM: Artificial Sequence
<220> FEATURE:
<223> OTHER INFORMATION: example of the silently mutated CDS

<400> SEQUENCE: 21
atcttagata ac                                                            12
```

-continued

```
<210> SEQ ID NO 22
<211> LENGTH: 12
<212> TYPE: DNA
<213> ORGANISM: Artificial Sequence
<220> FEATURE:
<223> OTHER INFORMATION: example of the silently mutated CDS

<400> SEQUENCE: 22
atcgtacatc ta                                                         12
```